US009821000B2

(12) United States Patent
Ferreira et al.

(10) Patent No.: US 9,821,000 B2
(45) Date of Patent: Nov. 21, 2017

(54) COMPOUNDS, COMPOSITIONS AND CORRESPONDING USES FOR PREVENTING AND/OR TREATING OF DYSLIPIDEMIA

(71) Applicants: CENTRE NATIONAL DE LA RECHERCHE SCIENTIFIQUE (CNRS), Paris (FR); UNIVERSITE DE POITIERS, Poitiers (FR)

(72) Inventors: Thierry Ferreira, Iteuil (FR); Romain Ferru-Clement, Poitiers (FR); Clarisse Vandebrouck, Poitiers (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 0 days.

(21) Appl. No.: 15/027,738

(22) PCT Filed: Oct. 8, 2014

(86) PCT No.: PCT/EP2014/071543
§ 371 (c)(1),
(2) Date: Apr. 7, 2016

(87) PCT Pub. No.: WO2015/052237
PCT Pub. Date: Apr. 16, 2015

(65) Prior Publication Data
US 2016/0287542 A1 Oct. 6, 2016

(30) Foreign Application Priority Data
Oct. 8, 2013 (FR) ...................................... 13 02334

(51) Int. Cl.
A61K 31/7024 (2006.01)
A61K 31/201 (2006.01)
(Continued)

(52) U.S. Cl.
CPC .......... A61K 31/7024 (2013.01); A23L 33/12 (2016.08); A61K 31/164 (2013.01);
(Continued)

(58) Field of Classification Search
CPC .. A61K 31/201; A61K 31/164; A61K 31/231; A61K 31/7024; A23L 33/12
See application file for complete search history.

(56) References Cited

U.S. PATENT DOCUMENTS

2003/0066100 A1* 4/2003 Machaty .............. C12N 5/0609
800/17
2009/0124608 A1* 5/2009 Prather ................ A61K 31/454
514/230.5

FOREIGN PATENT DOCUMENTS

EP 0104043 A2 3/1984
WO 02083059 A2 10/2002
(Continued)

OTHER PUBLICATIONS

International Search Report for PCT/EP2014/071543 dated Mar. 2, 2015.
(Continued)

Primary Examiner — Yate K Cutliff
(74) Attorney, Agent, or Firm — Thomas | Horstemeyer LLC

(57) ABSTRACT

The present invention relates to the field of medicine. It relates more particularly to the use of compounds to prevent and/or treat lipotoxicity in a subject, especially lipotoxicity by hypoxia. The invention relates more particularly to compositions, especially pharmaceuticals compositions and nutritional supplements or complements comprising such compounds as well as their use to prevent and/or treat lipotoxicity, especially lipotoxicity by hypoxia. The compounds and compositions of the invention can especially be advantageously used to prevent and/or treat a pathology
(Continued)

from among pulmonary pathologies, especially cystic fibrosis or a chronic obstructive pulmonary disease.

12 Claims, 11 Drawing Sheets

(51) Int. Cl.
| | |
|---|---|
| A61K 31/231 | (2006.01) |
| A61K 45/06 | (2006.01) |
| A23L 33/12 | (2016.01) |
| A61K 31/232 | (2006.01) |
| A61K 31/357 | (2006.01) |
| A61K 31/661 | (2006.01) |
| A61K 31/7032 | (2006.01) |
| A61K 31/164 | (2006.01) |

(52) U.S. Cl.
CPC .......... *A61K 31/201* (2013.01); *A61K 31/231* (2013.01); *A61K 31/232* (2013.01); *A61K 31/357* (2013.01); *A61K 31/661* (2013.01); *A61K 31/7032* (2013.01); *A61K 45/06* (2013.01); *A23V 2002/00* (2013.01)

(56) References Cited

FOREIGN PATENT DOCUMENTS

| | | |
|---|---|---|
| WO | 2010149170 A1 | 12/2010 |
| WO | 2012054527 A2 | 4/2012 |

OTHER PUBLICATIONS

Stone Virginia M et al: "The cytoprotective effects of oleoylethanolamide in insulin-secreting cells do not require activation of GPR119." British Journal of Pharmacology, vol. 165. No. 8. Apr. 2012 (Apr. 2012), pp. 2758-2770, XP002721326, ISSN: 1476-5381.

Morgan N G et al: "Unsaturated fatty acids as cytoprotective agents in the pancreatic <2>-cell", Prostaglandins Leukotrienes and Essential Fatty Acids, vol. 82. No. 4-6, Apr. 1, 2010 (Apr. 1, 2010), pp. 231-236, XP027022275, Churchill Livingstone. Edinburgh, ISSN: 0952-3278, DOI: 10.1016jj.

Pineau Ludovic et al: "Lipid-induced ER stress: synergistic effects of sterols and saturated fatty acids.", Traffic (Copenhagen. Denmark), vol. 10, No. 6, Jun. 2009 (Jun. 2009), pp. 673-690, XP002733951, ISSN: 1600-0854.

Laurie-Anne Payet et al: "Saturated FattyAcids Alter the Late Secretory Pathway by Modulating Membrane Properties", Traffic, vol. 14, No. 12, Dec. 2, 2013 (Dec. 12, 2013), pp. 1228-1241, XP055159381, ISSN: 1398-9219, DOI: 10.1111/tra.12117.

Payet Laurie-Anne et al: 11 Cystic fibrosis bronchial epithelial cells are lipointoxicated by membrane palmitate accumulation., PLoS One, vol. 9, No. 2, E89044, 2014, pp. 1-12, XP002733952, ISSN: 1932-6203. DOI: 10.1093jglycobjcwt056.

Alkhateeb H, et al. (2007); Two phases of palmitate-induced insulin resistance in skeletal muscle: impaired GLUT4 translocation is followed by a reduced GLUT4 intrinsic activity. American Journal of Physiology—Endocrinology and Metabolism 293: E783-E793, 12 pages.

Bigay, et al. ArfGAP1 responds to membrane curvature through the folding of a lipid packing sensor motif. The EMBO Journal; Jul. 6, 2005;24 (13): pp. 2244-2253; www.embojournal.org.

Boslem E., et al.; A lipidomic screen of palmitate-treated MIN6 β-cells links sphingolipid metabolites with endoplasmic reticulum (ER) stress and impaired protein trafficking. www.Biochem.org; Apr. 1, 2011; 435(1): pp. 267-276.

Butler AE, et al.; (2003) β-Cell Deficit and Increased β-Cell Apoptosis in Humans With Type 2 Diabetes. vol. 52, pp. 102-110.

Cnop M, et al.; (Aug. 2001) Inverse Relationship Between Cytotoxicity of Free Fatty Acids in Pancreatic Islet Cells and Cellular Triglyceride Accumulation. Diabetes vol. 50: pp. 1771-1777.

Cunha DA, et al.; (2008) Initiation and execution of lipotoxic ER stress in pancreatic β-cells. Journal of Cell Science; vol. 121, pp. 2308-2318.

Deguil, J, et al.; (2011) Modulation of Lipid-Induced ER Stress by Fatty Acid Shape. Traffic 2011, John Wiley & Sons; 12: pp. 349-362.

Dhayal S, et al.; (2011) Structure-activity relationships influencing lipid-induced changes in eIF2{alpha} phosphorylation and cell viability in BRIN-BD11 cells. FEBS Letters; 585: pp. 2243-2248.

Diakogiannaki, E., et al.; (2008) Differential regulation of the ER stress response by long-chain fatty acids in the pancreatic βcell. Molecular Mechanisms of Glucolipotoxicity in Diabetes; 959 vol. 036, pp. 959-962.

Diakogiannaki E, Welters HJ, Morgan NG. (2008) Differential regulation of the endoplasmic reticulum stress response in pancreatic {beta}-cells exposed to long-chain saturated and monounsaturated fatty acids. vol. 197, pp. 553-563.

Egnatchik, RA, et al.; ER calcium release promotes mitochondrial dysfunction and hepatic cell lipotoxicity in response to palmitate overload; Molecular Metabolism; May 22, 2014; 3(5): pp. 544-553.

Guo, W, et al.; (2007) Palmitate modulates intracellular signaling, induces endoplasmic reticulum stress, and causes apoptosis in mouse 3T3-L1 and rat primary preadipocytes; Am J Physiol Endocrinol Metab 293: E576-E586, 2007; First published Jun. 5, 2007; vol. 293, pp. E576-E586.

Kato T, et al.; (2008) Palmitate Impairs and Eicosapentaenoate Restores Insulin Secretion Through Regulation of SREBP-1c in Pancreatic Islets. vol. 57, pp. 2382-2392.

Katsoulieris, E, et al.; (2009) [alpha]-Linolenic acid protects renal cells against palmitic acid lipotoxicity via inhibition of endoplasmic reticulum stress. European Journal of Pharmacology 623: pp. 107-112.

Kincaid MM, Cooper AA (2007) ERADicate ER Stress or Die Trying. Antioxid Redox Signal; vol. 9, No. 12, 16 pages.

Kirby EF, et al.; Enhancing the Potency of F508del Correction: A Multi-Layer Combinational Approach to Drug Discovery for Cystic Fibrosis. J Pharmacol ClinToxicol. Aug. 28, 2013;1(1):1007; 14 pages.

Kohlwein SD, Petschnigg J (2007) Lipid-induced cell dysfunction and cell death: lessons from yeast. Current hypertension reports9: 455-461.

Laybutt, DR, Preston AM, et al. ; (2007) Endoplasmic reticulum stress contributes to beta cell apoptosis in type 2 diabetes. Diabetologia vol. 50: pp. 752-763.

Listenberger, LL; et al.; (2003) Triglyceride accumulation protects against fatty acid-induced lipotoxicity. PNAS 100: 3077-3082.

Patil, CK, et al. Gcn4p and novel upstream activating sequences regulate targets of the unfolded protein response. PLoS Biology, Aug. 2004; 2(8): E246; 16 pages.

Pedemonte, N, et al.; Small-molecule correctors of defective ΔF508-CFTR cellular processing identified by high-throughput screening; The Journal of Clinical Investigation;. Sep. vol. 115(9): pp. 2564-2571. 2005.

Petschnigg J, Moe OW, Stagljar I (2011) Using yeast as a model to study membrane proteins. Current opinion in nephrology and hypertension 20: pp. 425-432.

Petschnigg J, Wolinski H, Kolb D, Zellnig Gn, Kurat CF, Natter K, Kohlwein SD (2009) Good Fat, Essential Cellular Requirements for Triacylglycerol Synthesis to Maintain Membrane Homeostasis in Yeast. J Biol Chem284: pp. 30981-30993.

Pineau, L., et al,; (2008) A Lipid-mediated Quality Control Process in the Golgi Apparatus in Yeast; Molecular Biology of the Cell; vol. 19: pp. 807-821.

Poon PP, et al.; The Gcs1 and Age2 ArfGAP proteins provide overlapping essential function for transport from the yeast trans-Golgi network; The Journal of Cell Biology; Dec. 24, 2001; 155(7): pp. 1239-1250.

(56) References Cited

OTHER PUBLICATIONS

Robinston, M., et al; The Gcs1 Art-GAP mediates Snc1,2 v-SNARE retrieval to the Golgi in yeast. Molecular Biology of the Cell. Apr. 2006; 17(4): pp. 1845-1858.

Sampson HM, et al; Identification of a NBD1-binding pharmacological chaperone that corrects the trafficking defect of F508del-CFTR; Chemistry and Biology; Feb. 25;18(2): pp. 231-242. 2011.

Schneider, MF, et al.; Network formation of lipid membranes: triggering structural transitions by chain melting. ProcNatlAcadSci U.S.A. Dec. 7, 1999; 96(25): pp. 14312-14317.

Stein DT, et al; (1997) The insulinotropic potency of fatty acids is influenced profoundly by their chain length and degree of saturation. The Journal of Clinical Investigation 100: pp. 398-403.

Van Goor, F, et al. Rescue of ΔF508-CFTR trafficking and gating in human cystic fibrosis airway primary cultures by small molecules; . Am J Physiol Lung Cell Mol Physiol. Jun.; 290(6): L1117-30. 2006; 14 pages.

Van Goor, F, et al; Correction of the F508del-CFTR protein processing defect in vitro by the investigational drug VX-809. ProcNatlAcadSci U.S.A. Nov. 15; 108(46): pp. 18843-18848. 2011.

Wang, Y, et al; Specific rescue of cystic fibrosis transmembrane conductance regulator processing mutants using pharmacological chaperones. Molecular Pharmacology; Jul.;70(1): pp. 297-302. 2006.

Wei Y, et al.; (2006) Saturated fatty acids induce endoplasmic reticulum stress and apoptosis independently of ceramide in liver cells. vol. 291, p. E275-E281.

Zhang K; (2006) The unfolded protein response: A stress signaling pathway critical for health and disease. AAN Enterprises, Inc; vol. 66, pp. S102-S109.

Vachel, L, et al.; Effect of VX-770 (ivacaftor) and OAG on Ca2+ influx and CFTR activity in G551D and F508del-CFTR expressing cells. Journal of Cystis Fibrosis; Dec. 2013; 12(6): pp. 584-591.

* cited by examiner

A

Oleic acid  OAG  LPA

B

COMPOUNDS, COMPOSITIONS AND CORRESPONDING USES FOR PREVENTING AND/OR TREATING OF DYSLIPIDEMIA

CROSS-REFERENCE TO RELATED APPLICATION

This application is the 35 U.S.C. §371 national stage application of PCT Application No. PCT/EP2014/071543, filed Oct. 8, 2014, which claims priority to and the benefit of, FR Patent Application No. 1302334, filed Oct. 8, 2013, both of which are herein incorporated by reference in their entirety.

FIELD OF THE INVENTION

The present invention relates to the field of medicine. It relates more particularly to the use of compounds to prevent and/or treat lipotoxicity in a subject, especially lipotoxicity by hypoxia. Lipotoxicity, or dyslipidemia in its broad sense, is typically related to the presence in excess of fatty acids, especially saturated long-chain fatty acids, and/or sterols in the biological membranes, including the biological membranes of non-adipocyte cells. The invention relates more particularly to compositions, especially pharmaceuticals compositions and nutritional supplements or complements, comprising such compounds as well as their use for preventing and/or treating lipotoxicity, especially lipotoxicity by hypoxia. The compounds and compositions of the invention can especially be advantageously used to prevent and/or treat pathologies from among pulmonary pathologies, especially cystic fibrosis or a chronic obstructive pulmonary disease.

PRIOR-ART SOLUTIONS

Cystic fibrosis is a disease affecting especially the glandular epithelia of many organs. This lethal genetic disease with recessive autosomal transmission is linked to mutations in the CFTR (cystic fibrosis transmembrane conductance regulator) gene located in chromosome 7, leading to the deterioration of the CFTR protein. More than 1,900 different mutations have been identified so far. The most frequent mutation is the "F508del-CFTR" (ΔF508) mutation in which three nucleotides are deleted at the level of the tenth exon of the gene, leading to the elimination of an amino acid, phenylalanine, at position 508. The dysfunction of the CFTR protein prompts especially an increase in the viscosity of the mucous and its accumulation in the respiratory and digestive tracts. From a clinical viewpoint, the most frequent form associates respiratory, digestive and height-weight growth disorders. Pulmonary disorders are the major cause of morbidity and mortality. Cystic fibrosis leads to chronic inflammation of the bronchi with bacterial superinfection, leading to the gradual deterioration of the respiratory condition, which develops through successive attacks, starting with symptoms such as coughing and ending in severe respiratory insufficiency. Various symptomatic palliative treatments are available—these include physiotherapy, antibiotherapy, administration of mucolytics. However, there is no curative treatment as yet, whether medicinal or using a gene therapy protocol. The only medicine currently being marketed is Ivacaftor® comprising a molecule that potentiates the CFTR protein among chronic cystic fibrosis subjects carrying the G551D mutation. Besides, several pharmacological and/or clinical studies on molecules of therapeutic interest have been reported. These candidate molecules are generally aimed at correcting, regulating, potentializing and/or chaperoning the dysfunctional CFTR protein (cf. for example Kirby et al., 2014; Pedemonte et al., 2005; Van Goor et al., 2006; Wang et al., 2006; Sampson et al., 2011; Van Goor et al., 2011). Some of these molecules are aimed especially at correcting the misfolding defect in the protein F508del-CFTR, which prevents it from acquiring a proper three-dimensional conformation, progressing along the secretory channel, and accessing its destination site, namely the plasma membrane. However, the great majority of these candidate molecules suffer from a lack of efficacy in in vivo studies and/or clinical trials.

Chronic obstructive pulmonary diseases (COPDs) cover several systemic chronic illnesses of respiratory origin and affect the bronchi. The main cause of this disease is smoking. COPD is characterized especially by a slow and gradual obstruction of the air passages and the lungs, associated with permanent distension of the pulmonary alveoli. From a clinical viewpoint, COPDs are associated with respiratory disorders, with possible neurological, cardiovascular or muscular complications. COPDs especially lead to respiratory insufficiencies which can be severe. There are various symptomatic palliative treatments available, such as antibiotic treatment, corticosteroid therapy, the use of bronchial dilators or mechanical ventilator supports or even long-term oxygen therapy for the most severe forms of this disease.

Recent research has shown that bronchial epithelial cells freshly dissociated from biopsies of cystic fibrosis patients show an abnormally high accumulation of palmitic acid (SFA) within phosphatidylcholines (PC) of the cell membranes (cf. Payet et al., 2014). Previously, it had been established that the conversion of endogenous cell SFA into UFA is catalyzed by oxygen-dependent enzymes (Pineau et al., 2008; Pineau et al., 2009). Thus, after having shown that hypoxia is induced in the biopsies of patients with cystic fibrosis or, conversely, that hypoxia leads to lipotoxicity in bronchial epithelial cells, in vitro (cf. Payet et al., 2014), it was concluded that the bronchial epithelial cells of patients with cystic fibrosis were subject to lipotoxicity through an accumulation of palmitic acid caused by hypoxia. Besides, the inventors have also been able to carry out observations of the same type, linking hypoxia to lipotoxicity, on pseudo-healthy biopsies of smokers affected by lung cancer (these biopsies were taken from outside the cancer-affected pulmonary zone).

As broadly understood, dyslipidemia (or lipotoxicity) is defined especially as an abnormally high or abnormally reduced concentration of lipids, typically free or non-esterified fatty acids, sterols (for example cholesterol, triglycerides or phospholipids in blood). Dyslipidemia is defined then as a deregulation of lipid homeostasis.

Non-esterified fatty acids (NEFA) or free fatty acids (FFA) represent a major energy element of the organism. They are constituted by a complex mixture of fatty acids that differ by their number of double bonds and the number of carbon atoms constituting their hydrocarbon chain. Of endogenous origin, they are formed by biosynthesis in the cytoplasm of the cells and are used in the form of acyl-coA to synthesize triglycerides in the adipose tissues and the liver especially.

In plasma, there are mainly four fatty acids that represent 85% of NEFA: they are oleic acid, palmitic acid, linoleic acid and stearic acid. The majority of the NEFAs are linked to albumen. They come from triglycerides of the fatty tissue which get hydrolyzed during fasting, under the effect of tissue and blood lipoprotein lipase, into glycerol and fatty acids. Their concentration varies in high proportions depending on age, food intake and physical exercise. Their release is generally stopped during post-prandial periods.

A sterol is a lipid possessing a sterane core, of which the carbon 3 is a carrier of a hydroxide group. Sterols are considered to be a sub-class of steroids. Cholesterol, one of the most common and widespread sterols, is vital for cell operation and is a precursor of vitamins and of fat-soluble steroid hormones.

Typically, as broadly understood, dyslipidemia at the cell level corresponds to an abnormally high concentration of lipids in the biological membranes and especially an accumulation of saturated fatty acids (SFAs) in the biological membranes. The term "cell dyslipidemia" is also used. Such an accumulation of SFA in the biological membranes leads to an overall disturbance of membrane plasticity at the cell level. This phenomenon is known as lipotoxicity. Established lipotoxicity is responsible for disturbance of all the membrane mechanisms (detectable at every step in the protein secretion pathway). In humans, all cells can thus be concerned by lipotoxicity with the exception of adipocytes, which alone are capable of synthesizing neutral lipids and storing them).

Until now, only the unsaturated fatty acids (UFA), especially oleic acid (olive oil) were known to counter the deleterious effects of intoxication related to the accumulation of SFAs (Cunha et al., 2008; Diakogiannaki et al., 2008; Katsoulieris et al., 2009; Pineau et al., 2009; Stein et al., 1997; Wei et al., 2006; Deguil et al., 2011). However, their use as nutraceuticals and/or medicines comes up against two major limits. On the one hand, UFAs essentially have preventive properties and are therefore of limited interest in the context of the treatment of established lipotoxicity, i.e. lipotoxicity responsible for a disturbance of all the membrane mechanisms (detectable all the steps of the protein secretory pathway). Indeed, UFAs act by entering into direct competition with SFAs during food intake, in the synthesis of membrane phospholipids (PL). On the other hand, the toxicity of UFAs has been demonstrated on cells incapable of converting (buffering) and then storing excess free fatty acids, especially UFAs, as neutral lipids, typically triglycerides (TG) and/or esterified sterols. This is the case for example for a yeast strain where, owing to the absence of the four acyltransferase enzymes Lro1p, Dga1p, Are1p and Are2p, a deregulation of the neutral lipid synthesis is observed. During exposure of this mutant strain to an exogenous source of UFA, the lipid deregulation is expressed by a massive proliferation of intra-cell membranes and then the death of the cells by a process independent of the UPR (unfolded protein response; see here below) (Kohlwein & Petschnigg, 2007; Petschnigg et al., 2011). Interestingly, identical phenomena were observed in the cells of mammals (Listenberger et al., 2003). This explains why unsaturated fatty acids become toxic for cells when these cells have already undergone lipointoxication conditions. This is a state in which the capacity of the cell to store unsaturated fatty acids in the form of neutral lipids is exceeded (the lipo-intoxicated cell is qualified as a "metabolically inactive" cell). Alternatively, under normal conditions, an identical phenomenon has also been observed for cells having very low TG synthesizing capacity, for example pancreatic non-beta cells (Cnop M et al., 2001). In humans, except for the adipocytes (which are the only cells capable of synthesizing neutral lipids and storing them), all cell types are thus liable to be subject to lipotoxicity. It is especially known that disturbances related to the accumulation of SFA leads to apoptosis of pancreatic β cells responsible for insulin synthesis (Butler et al., 2003) or to apoptosis of the hepatocytes (Egnatchik et al., 2014).

Thus, as mentioned here above, there is no current therapeutic strategy aimed at basically restoring the functions of the lipo-intoxicated cells and organs and therefore no such strategy capable of acting at the early stages of the cascade of deleterious effects encountered in pulmonary pathologies leading especially to respiratory failure, typically upstream to each of the steps targeted by existing treatment. In addition, research by the inventors shows that not taking account of the lipotoxicity context, in the framework of pulmonary pathologies especially, and of cystic fibrosis in particular, could be responsible for a technological limitation and could explain the absence of curative treatment up to now.

The inventors shall now describe the molecules or compounds, and compositions comprising such molecules or compounds, used to prevent the emergence of lipotoxicity within biological membranes, typically the cell accumulation of fatty acids, especially saturated fatty acids, or to treat established lipotoxicity by acting on the phenomenon commonly impaired in all lipo-intoxicated tissues namely membrane plasticity.

GOALS OF THE INVENTION

The present invention is aimed at overcoming the drawbacks of the prior art, explained especially here above.

In particular, it is a goal of the invention, in at least one embodiment, to prevent or to treat lipotoxicity by hypoxia in a subject. The invention is thus especially aimed at preventing and/or treating, in a subject, lipotoxicity by hypoxia related to the presence in excess of saturated fatty acids and/or sterols in non-adipocyte biological cell membranes.

It is another goal of the invention, according to at least one embodiment, to prevent and or treat pulmonary pathology in a subject, especially pulmonary pathology leading to respiratory failure, more particularly a pulmonary pathology that is cystic fibrosis or a chronic obstructive pulmonary disease. The invention is thus aimed especially at preventing and/or treating cystic fibrosis. The invention is also aimed in particular at preventing and/or treating chronic obstructive pulmonary diseases.

It is another goal of the invention according to at least one embodiment, to limit or even to prevent dysfunction or apoptosis of non-adipocyte cells, lipo-intoxicated by hypoxia, associated especially by the diminishing or elimination of the fluidity of their plasma membrane and/or the membrane of their organelles.

It is another goal of the invention, according to at least one embodiment, to provide a compound capable of preventing and/or treating lipotoxicity by hypoxia in a subject, while at the same time being non-toxic for cells incapable of synthesizing neutral lipids, typically triglycerides and/or esterified sterols. The invention is aimed especially at providing a compound capable of preventing and/or treating lipotoxicity by hypoxia in a subject, this compound being an alternative to or even superior to oleic acid in its properties while at the same time being non-toxic. The invention is thus aimed especially at providing a compound capable of preventing and/or treating lipotoxicity by hypoxia in a subject while at the same time being non-toxic for the bronchial epithelial cells.

SUMMARY OF THE INVENTION

These goals as well as others that shall appear more clearly here below are achieved by means of compounds, compositions and corresponding uses, according to the present invention.

The invention pertains to a new class of molecules intended for the prevention and/or the treatment of pathologies associated with lipotoxicity by fatty acids, typically saturated long-chain and/or trans fatty acids. The term long-chain fatty acids is understood typically to mean fatty acids for which the carbon chain comprises at least 14 carbon atoms, typically between 14 and 24 carbon atoms, for example 16 or at least 18 carbon atoms, typically between 14 and 22 or between 14 and 18 carbon atoms.

Lipotoxicity can take the form of a reversal of the SFA/UFA (unsaturated fatty acid) ratio in the phospholipids present within biological membranes, the SFA becoming predominantly present or even completely replacing the UFA.

The molecules of the invention can be intended for the prevention and/or the treatment of dyslipidemia, metabolic syndrome, a syndrome or an anomaly characteristic of metabolic syndrome, preferably the prevention and/or treatment of type 2 diabetes.

The molecules of the invention can be intended for the prevention and/or treatment of lipotoxicity of endogenous origin (or "endogenous" lipotoxicity), especially lipotoxicity by hypoxia (or "hypoxic" lipotoxicity). The term "hypoxia" is understood to mean a mismatch between the oxygen requirements of the tissues and the inputs, leading to a state of insufficient oxygenation of certain cells, certain tissues and/or organs. Under conditions of normoxia, the proportions in $O_2$ and in $N_2$ are typically 95% and 5%. Thus, the molecules of the invention can be intended to prevent and/or treat a pulmonary pathology, especially a pulmonary pathology associated with respiratory failure, more particularly a pulmonary pathology associated with respiratory insufficiency chosen from among cystic fibrosis or COPDs.

Indeed, it is possible to distinguish between lipotoxicity of exogenous origin ("exogenous" lipotoxicity) and lipotoxicity of endogenous origin (or "endogenous" lipotoxicity). Exogenous lipotoxicity is induced by over-exposure of the cells to an environmental source of SFA. Endogenous lipotoxicity, for its part, is induced by deregulation of the endogenous balance between UFA and SFA. These forms of lipotoxicity appear especially when a cell is no longer capable of controlling or regulating its fatty acid content, in space or in time, according to the requirements of balance between SFA and UFA, and constraints of membrane plasticity specific to an endomembrane compartment considered. By means of a yeast cell model cultivated under conditions that mimic hypoxia, the inventors have demonstrated that yeasts accumulate SFA (for example by non-conversion of the endogenous SFA into UFA) and that the induced lipotoxicity causes a certain number of deleterious effects, such as stress on the endoplasmic reticulum, a triggering of the UPR (unfolded protein response), a defect of vesiculation and a defect of vesicular traffic in the distal phases of the protein secretory pathway.

The starting point of the inventors was the observation that the clinical tables of patients suffering from cystic fibrosis and COPD share a certain number of similarities. These common points include (1) an exacerbation of inflammation in the pulmonary tissues, (2) congestion in the respiratory channels related to the deterioration of the rheological properties of the mucus, (3) high predisposition to the triggering of apoptosis and (4) bronchial hypertension. The inventors associated these different points with the presence of lipotoxicity with SFA and they proposed, relative to the literature, that this characteristic can be the key element from which all the symptoms arise. In order to confirm this assumption, and in order to identify a possible therapeutical solution, the inventors then conducted a certain amount of experimental research.

In a first stage, the lipotoxicity of freshly dissociated bronchial tissues, especially by palmitic acid, was brought to light by analysis of the fatty acid content of the purified phospholipids, using biopsies of healthy bronchial tissues or of tissues obtained from patients affected by cystic fibrosis or COPD. In addition, it was proposed that this state can be correlated with conditions of respiratory failure and hypoxia on the basis of the mode of action of the intra-cell desaturases, enzymes implicated in the conversion of endogenous SFA into UFA that are oxygen-dependent.

In a second stage, these conclusions were validated by means of an in vitro model artificially reconstituting the lipotoxicity observed in the biopsies on patients. This model validated the involvement of respiratory insufficiency and, especially, hypoxia in the induction of forms of lipotoxicity by SFA in the bronchial epithelium.

In a third stage, it was observed that the lipotoxicity of bronchial epithelial cells by palmitic acid activated the UPR process and ultimately apoptosis. The inventors also demonstrated that the compounds and compositions according to the present invention significantly inhibit the triggering of apoptosis and that these compounds are therefore useful for preventing and/or treating lipotoxicity, especially lipotoxicity by hypoxia. In this respect, these compounds and compositions according to the invention can especially be advantageously used to prevent and/or treat a pathology chosen from among the pulmonary pathologies, especially cystic fibrosis or chronic obstructive pulmonary diseases.

Secondarily, the inventors have shown that the compounds and compositions according to the present invention exert an effect on the bronchi of patients affected by cystic fibrosis or COPD. In this respect, the compounds and compositions according to the invention can especially be advantageously used to prevent and/or treat bronchial hypertension associated with pulmonary pathologies especially cystic fibrosis or chronic obstructive pulmonary disorders.

A considerable advantage that the molecules (or compounds) of the invention have over the UFA, and especially oleic acid, used in the prior art to compensate for excess SFA is that, contrary to these latter elements, they do not cause any cell toxicity and especially no toxicity in cells incapable of synthesizing neutral lipids, especially non-adipocyte cells, for example pancreatic cells or bronchial epithelial cells.

The molecules of the invention have another major advantage in that, contrary to the UFA used preventively in the prior art, they can also be used therapeutically because of their capacity to restore cell function, for example by acting on membrane plasticity. They can thus advantageously be used to treat established lipotoxicity, i.e. lipotoxicity responsible for detectable cell dysfunction, typically responsible for deterioration of the cell's capacity or even for its incapacity to carry out its membrane vesiculation functions and vesicular traffic, which are fundamental mechanisms in intra-cell communication between compartments and indispensable to the life of the cells.

One particular object of the invention thus relates to a compound comprising a polar head, comprising at least one hydroxyl residue, on which there is grafted a unique unsaturated fatty acid comprising between 16 and 24, for example between 16 and 22 or between 16 and 20 carbon atoms and having 1 to 6, for example 3, unsaturations in cis configuration for a use to prevent and/or treat lipotoxicity by hypoxia in a subject.

Dyslipidemia—or lipotoxicity—typically affects the biological membranes, including the biological membranes of non-adipocyte cells. In the present application, the term "dyslipidemia" in its broad sense and the term "lipotoxicity" are used interchangeably. Dyslipidemia—or lipotoxicity—is generally related to the presence of fatty acids and/or sterols in excess in said biological membranes. The fatty acids are especially saturated long-chain fatty acids. The quantity of SFAs and/or sterols is especially deemed to be excessive when, for example, it prompts cell dysfunction by degrading membrane plasticity.

Another object of the invention relates to a compound whose polar head is of formula (I):

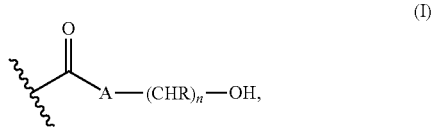

wherein:
A is a nitrogen or oxygen atom, preferably and oxygen atom,
n is equal to 2 or 3, preferably n equals 2, and
R is any chemical grouping whatsoever,
for a use to prevent and/or treat lipotoxicity in a subject, typically a lipotoxicity as defined here above.

In one particular embodiment, the compounds of interest that can be used in the context of the invention are chosen for example from among 1-oleoyl-2-acetyl-sn-glycerol, 1-oleoyl-sn-glycerol-3-phosphate, 2-arachidonoyl glycerol, mannide monooleate, 3-hydroxy-2,2-bis(hydroxymethyl) propyl oleate, N,N-diethanololeamide, propylene glycol monooleate, 1-oleoyl glycerol, 2-oleoyl glycerol, oleic acid monoester with triglycerol, 9-octadecenoic Acid (Z)-(2,2-Dimethyl-1,3-dioxolan-4-yl)methyl ester, diethylene glycol monooleate, and their mixtures; preferably from amongst 1-oleoyl-2-acetyl-sn-glycerol (OAG), 1-oleoyl-sn-glycerol-3-phosphate (1-oleoyl lysophosphatidic acid or LPA), 2-arachidonoyl glycerol (2-AG), mannide monooleate, 3-hydroxy-2,2-bis(hydroxymethyl)propyl oleate, N,N-diethanololeamide, propylene glycol monooleate, oleic acid monoester with triglycerol and (9-octadecenoic acid (Z)-(2, 2-Dimethyl-1,3-dioxolan-4-yl)methyl ester, and their mixtures.

In another particular embodiment, the compounds of interest according to the invention are selected from among mannide monooleate, le 3-hydroxy-2,2-bis (hydromethyl) propyl oleate, N,N-diethanololeamide, and their mixtures; alternatively N,N-diethanololeamide; alternatively mannide monooleate, 3-hydroxy-2,2-bis (hydromethyl)propyl oleate, and their mixtures.

In another particular embodiment, the compounds of interest that can be used in the context of the invention to prevent and/or treat lipotoxicity are chosen from among 1-oleoyl glycerol, 2-oleoyl glycerol, propylene glycol monooleate and oleic acid monoester with triglycerol, and their mixtures; preferably propylene glycol monooleate and oleic acid monoester with triglycerol, and their mixtures.

The invention also relates to a compound as described in the present invention for a use to prevent and/or treat a pulmonary pathology in a subject, especially a pulmonary pathology leading to respiratory failure, more particularly a pulmonary pathology that is cystic fibrosis or a chronic obstructive pulmonary disease.

The invention also relates to a compound taking the form of a pharmaceutical composition, a nutraceutical or a food supplement, comprising at least one compound according to the invention. One particular object typically pertains to a pharmaceutical composition comprising, in addition to said at least one compound according to the invention, at least one other compound (different from the compounds according to the invention) active on the therapeutical plane (and recognized as such by those skilled in the art).

The invention also relates to the use of such a composition to prevent and/or treat lipotoxicity by hypoxia in a subject, typically lipotoxicity by hypoxia in biological membranes, including biological membranes of non-adipocyte cells, especially lipotoxicity by hypoxia related to the presence in excess in certain biological membranes of fatty acids, more particularly saturated and/or trans long-chain fatty acids. It also relates to the use of such a composition to prevent and/or treat a pulmonary pathology in a subject, especially a pulmonary pathology leading to respiratory failure, more particularly a pulmonary pathology that is cystic fibrosis or a chronic obstructive pulmonary disease. The uses described can also be advantageously implemented in combination with at least one other therapeutically active compound (recognized as such by those skilled in the art and different from the compounds according to the invention) especially in the treatment of pulmonary pathologies, especially cystic fibrosis or COPD.

DETAILED DESCRIPTION

The inventors have shown that SFA coming from an exogenous source (food) or endogenous source (hypoxia or deterioration by mutation of the steps of desaturation of fatty acids) accumulate within the phospholipids constituting the cell membranes, thus disturbing numerous processes, by impairing the functions of the intra-cell organelles that play a role in the protein secretory pathway (cf. FIG. 1).

To make this demonstration, the inventors have developed a simple unicellular model (hem1Δ strain prepared out of bakers' yeast Saccharomyces cerevisiae) reproducing all the impacts of the SFA and of cholesterol observed in mammalian cells, especially all the anomalies involved in the development of metabolic syndrome (Pineau et al., 2008 and Pineau et al., 2009).

In a YPG medium (i.e. a medium that contains neither ergosterol (Erg) nor oleic acid (Ole)), the hem1Δ strain accumulates saturated fatty acids (especially palmitic acid, C16:0) in its phospholipids, especially phosphatidylcholine (PC). It must be noted that ergosterol is the sterol that is predominantly present in yeasts. In yeast, therefore, it constitutes the equivalent of cholesterol for humans.

The QM strain (Petschingg et al., 2009), in which the encoding genes for the enzymes responsible for the synthesis for triglycerides and esters of sterols have been deleted, is for its part incapable of converting an exogenous input of free fatty acids, of the oleic acid C18:1 type, into neutral lipids, so that this input leads to harmful stress owing to the disturbance of the balance of the membrane plasticity that it causes. The use of the QM strain has especially enabled the inventors to carry out tests of toxicity which have enabled a clear demonstration of the toxicity of the oleic acid in such circumstances (cf. FIG. 4).

More specifically, the inventors have observed the negative effects, in hem1Δ strains, of the accumulation of phospholipids carrying saturated chains (saturated PL) in membranes of the intra-cell organelles on the formation of the secretion vesicles. This lipotoxicity (which is endogenous because the cell system of the hem1Δ strains now synthesizes only SFAs) disturbs the lipid environment of the membrane of the endoplasmic reticulum (ER), impairs the process of folding (this is known as "misfolding") of the proteins and then triggers a complex response in said ER, a response known as "unfolded protein response" (UPR). A saturation of this failsafe system leads to a cell death by apoptosis. At the same time, the inventors have observed disturbances of the vesiculation of the Golgi apparatus as well as a deterioration of the traffic of reference proteins (example: Fur4p) between the Golgi apparatus and the plasma membrane. In concrete terms, the inventors have observed deterioration, due to lipotoxicity, of the entire secretory pathway. In other words, the hem1Δ strains of yeast has enabled them to confirm the impacts of the SFAs on RE stress as well as on the traffic of proteins towards the plasma membrane.

The endoplasmic reticulum (ER) is involved in several fundamental cell processes, including lipid synthesis, the regulation of calcium homeostasis and the synthesis of the proteins intended for the different organites and for the cell surface (for example the membrane proteins such as the ion channels and the transporters). The ER is also the site where the membrane or secreted proteins are assembled and folded. As a consequence, the UPR plays an essential role in maintaining the integrity and functions of the ER in enabling this organite to manage the accumulation of misfolded proteins (Kincaid & Cooper, 2007; Zhang & Kaufman, 2006). It must be noted that the toxicity of the SFAs is associated, in the pancreatic β-cells (responsible for the synthesis of insulin in mammals), with the induction of the UPR response (Cunha et al., 2008; Diakogiannaki & Morgan, 2008; Laybutt et al., 2007). In addition, Alkhateeb et al. (2007) and Kato et al. (2008) have observed that the accumulation of SFA impairs the addressing of the insulin receptor and of the glucose transporter Glut4 to the surface of the muscle cells.

Schneider et al. (1999) have observed that the membranes of the endoplasmic reticulum (ER) and of the Golgi apparatus are constituted primarily by unsaturated phospholipids (PL) while the level of saturated PLs increases gradually in the most distal compartments in the secretory pathway channel to reach its maximum at the plasma membrane. Major rates of unsaturated PL result in a high membrane fluidity, which is a crucial parameter for the recruitment of certain proteins essential to the formation of the vesicles. A classic example is provided by proteins of the Arf-GAP1 family, one of them being Gcs1p in yeast. It has been shown that Gcs1p is a mediator of the vesicular transport both between the Golgi apparatus and the ER, and between the ER and the plasma membrane (Robinson et al., 2006). Interestingly, the deletion of the GCS1 gene prompts a fragmentation of the Golgi apparatus and a disturbance of the post-Golgi vesicular traffic (Poon et al., 2001), which are phenomena that the inventors have themselves observed in the yeast model hem1Δ, i.e. in a condition of accumulation of SFA (cf. Payet et al, 2013.).

The proteins of the Arf-GAP1 family respond to the membrane curvature by getting adsorbed to the membrane surface via a specific motif called the ArfGAP1 Lipid Packing Sensor (ALPS; (Bigay et al., 2005)). Concretely, the ALPS motif does not recognize membrane curvature per se, i.e. as a curved geometry but recognizes loose packing of the polar heads of the phospholipids (loose lipid packing) which is a consequence of the membrane curvature (Bigay et al., 2005). The inventors have been able to show that the high rates of saturated PL in conditions of lipotoxicity are associated with an augmentation of the membrane lipid packing (Deguil et al., 2011), and that this augmentation impairs the recruitment by the Golgi apparatus of the Gcs1p coming from the cytoplasm (Payet et al., 2013). More generally, they have shown that the accumulation of fatty acids, especially SFAs, in biological membranes gave rise to the functional deregulation of the intra-cell organelles or organites, including the Golgi apparatus and the endoplasmic reticulum (ER), and especially a reduction of the rate of vesiculation responsible for a reduction of the translocation of certain membrane transporters and receptors on the cell surface.

The cell lipotoxicity brought about by the inventors results, in vitro, from exposure to an exogenous source of fatty acids exclusively in saturated form (exogenous lipotoxicity) or, alternatively, from an intrinsic incapacity of the cell to produce unsaturated forms of fatty acids ("endogenous" lipotoxicity).

Using their hem1Δ yeast model, the inventors have shown that oleic acid (Ole) in being metabolized in the phospholipids (PL) (cf. FIG. 1—loss of PL with SFA in return for PL with UFA) restores the plasticity of the membranes previously lipo-intoxicated by SFAs. Using the QM yeast strain, they have also shown that the beneficial effect observed is limited to cells having the capacity to buffer an excess of exogenous UFA in the form of neutral lipids. In cells that do not have this capacity, the surplus exogenous oleic acid ultimately leads to an abnormal proliferation of the intra-cell membranes which, in stressing the cells, will trigger their apoptosis.

The inventors have used their hem1Δ model and the QM strain to screen molecules of interest liable to prevent or limit the phenomenon, ideally to counter the toxic effect of saturated fatty acids present in excess and/or being poorly metabolized (i.e. esterified) and to correct all the disturbed phenomena. They have also discovered molecules capable especially of restoring cell function (by restoring for example membrane fluidity) to a level comparable to that found in non-pathological conditions.

The efficacy of the molecules pre-selected by the inventors, i.e. their capacity to restore cell function to a level comparable to that found in non-pathological conditions, even in the case of confirmed dyslipidemia, was then tested and demonstrated by the same inventors on pancreatic β-cells of mammals, especially in pancreatic β-cells of rats (BRIN-BD11 line).

The invention thus relates to a compound comprising a polar head, comprising at least one hydroxyl residue, on which there is grafted a single unsaturated fatty acid comprising 16 to 24, for example 16 to 20 and typically 18 carbon atoms and having 1 to 6, for example 3, unsaturation(s) in a cis configuration (identified in the present text as being a "compound of interest") for a use to prevent and/or treat lipotoxicity in a subject.

The subject concerned is an animal, typically a mammal, for example a mammal chosen from among mice, rats, pigs or human beings. The subject concerned is preferably a human being.

In the context of the present description, dyslipidemia—or lipotoxicity—the prevention and/or treatment of which is sought, typically affects the biological membranes, especially the biological membranes of non-adipocyte cells. It is generally related to the presence in excess, in said biological membranes, of fatty acids, especially saturated and/or trans long-chain fatty acids and/or sterols. Dyslipidemia—or lipotoxicity—is typically responsible for the poisoning of non-adipocyte cells causing dysfunction and/or the apoptosis of said cells by reducing or even eliminating the fluidity of their plasma membrane and/or the membrane of their organelles.

In one particular embodiment of the invention, the lipotoxicity is associated with the presence in the subject of a pulmonary pathology, particularly pulmonary pathology leading to respiratory insufficiency, more particularly a pulmonary pathology leading to a respiratory insufficiency that is cystic fibrosis or COPD.

It emerges from the present invention that the expression "presence in excess" of fatty acids, especially SFAs and/or sterols, is synonymous with lipotoxicity and designates the presence, in a non-adipocyte cell, in particular, of saturated fatty acids and/or trans fatty acids and/or sterols in a quantity sufficient to disturb the protein secretory pathway described further above and thus impair cell function (typically the protein secretory pathway and therefore the functioning of said proteins) or even, at a higher level, consequently impair the functioning of the corresponding organ.

At the cell level, lipotoxicity is diagnosed typically by the revealing of a modification of the fatty acid content of the PL of the biological membranes (at the level of the phospholipid species of phosphatidylcholine (PC) especially) and in particular by the depletion of the forms of PL with UFA to the benefit of PL with SFA. Just as in the operational mode described in the experimental part of the present description, such a lipidomic signature can be demonstrated following the extraction of the total cell lipids, the purification of their phospholipids and the analysis of these phospholipids by mass spectrometry (Deguil et al., 2011).

Besides, this cell lipotoxicity can be manifested by the induction of the UPR (unfolded protein response). As demonstrated by the experimental part, it is possible, in vitro, to detect and measure this UPR response by analysis of the expression of a reporter gene (such as the lacZ gene encoding for β-galactosidase, the enzyme activity of which can be quantified), this reporter gene containing in its promoter sequence one or more, for example four, elements of response to the specific UPR ("UPRE") of a gene characteristically induced during the triggering of said response, for example a gene chosen from among CHOP, BiP, GRP78 and ATF4 (Laybutt et al., 2007). Alternatively, the triggering of the UPR in response to lipotoxicity can be detected and measured by quantifying the proportion of active forms of certain key proteins in this cascade of cell events. This is the case with the protein eIF2α for which the abundance of the active phosphorylated form is proportional to the state of activation of UPR. As explained in the experimental part, the quantity of the active phosphorylated form can be evaluated by densitometry of the images obtained after Western blotting technique (Dhayal and Morgan, 2011).

In the context of the present invention, the UPR response can be advantageously detected or measured by detection or measurement of the expression of a gene or of the activity of a protein implicated in the UPR response as explained here above.

A compound of special interest is a compound as defined here above, the polar head of formula (I):

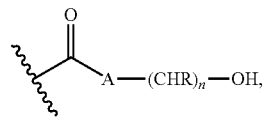

(I)

wherein:

A is typically an oxygen atom or an $NR_1$ group with $R_1=H$ or an alkyl in $C_1$-$C_6$ possibly substituted by an OH, and A is preferably an oxygen atom or NH or $NCH_3$ or $NCH_2CH_2OH$, and even more preferably, A is an oxygen atom, n=2 or 3, preferably n=2, and R is any chemical grouping and can be different from one grouping (CHR) to another.

In the formula (I), the bond interrupted by the zigzags represents the bond between the polar head and the carbon-comprising chain of the unsaturated fatty acid, the grouping C=O of the formula (I) being C=O of unsaturated fatty acid.

Preferably, R is a grouping comprising only carbon, hydrogen and oxygen atoms.

Preferably, R is a saturated grouping comprising only carbon, hydrogen and oxygen atoms.

Preferably, the radical $(CHR)_n$—OH is a derivative of glycerol, erythritol or a monosaccharide such as mannose.

In the present invention, each hydroxyl residue can be independently phosphated.

Two examples of compounds of interest that can be used in the context of the invention to prevent and/or treat lipotoxicity are identified here below:

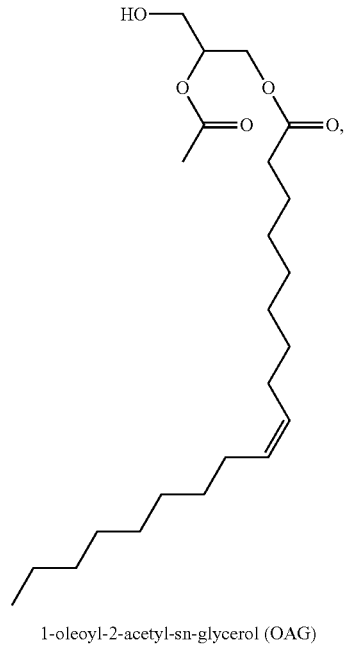

1-oleoyl-2-acetyl-sn-glycerol (OAG)

-continued
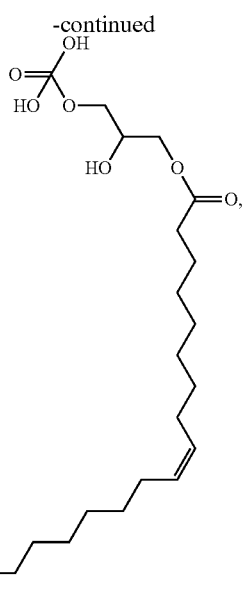
1-oleoyl-sn-glycerol-3-phosphate
((1-oleoyl lysophosphatidic acid or LPA)
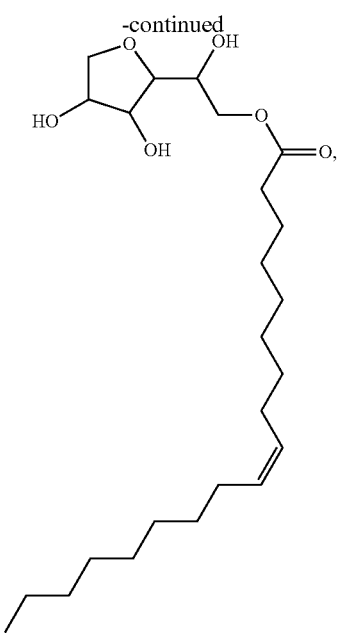
mannide monooleate
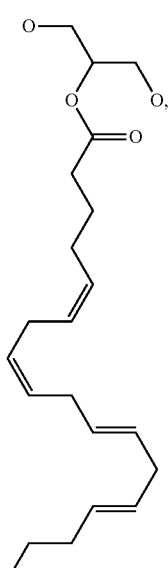
2-arachidonoyl glycerol (2-AG)
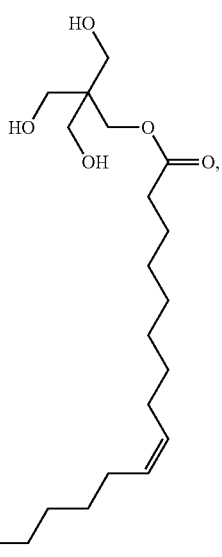
3-hydroxy-2,2-bis(hydroxymethyl)propyl oleate 15
-continued
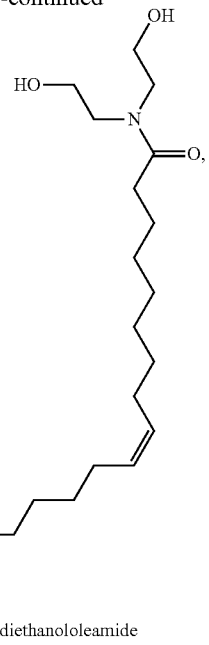
N,N-diethanololeamide
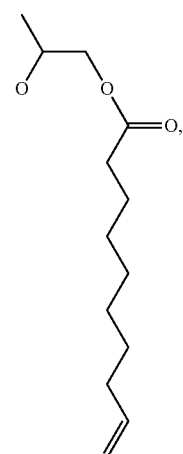
propylene glycol monooleate
16
-continued
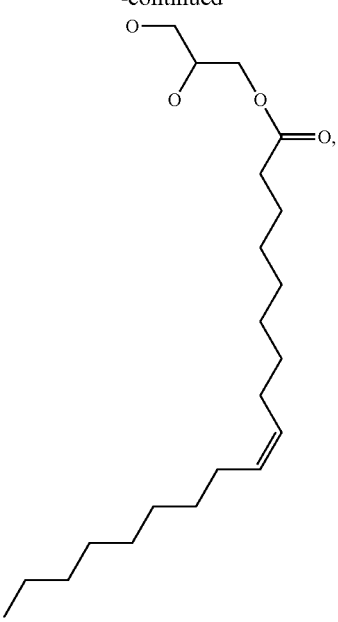
1-oleoyl glycerol
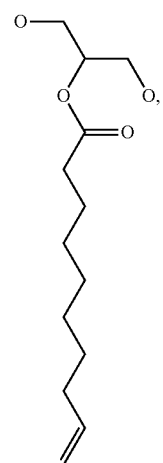
2-oleoyl glycerol -continued

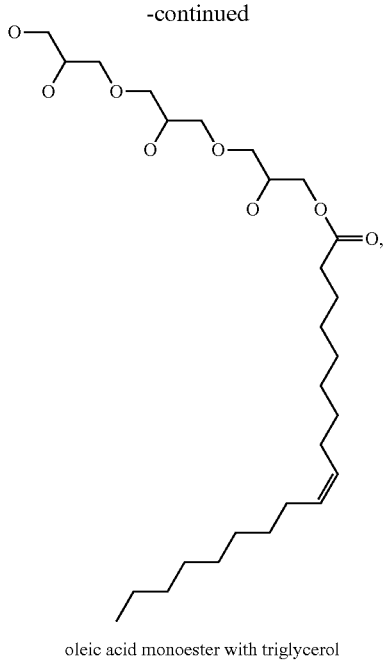

oleic acid monoester with triglycerol

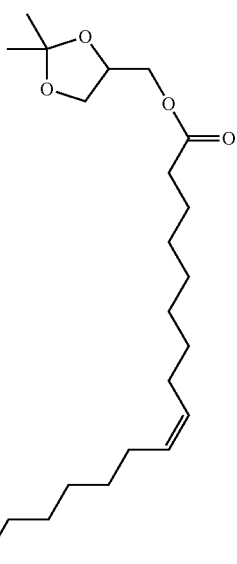

9-octadecenoic Acid (Z)-(2,2-Dimethyl-1,3-dioxolan-4-yl)methyl ester

-continued

Diethylene glycol monooleate

Compounds of interest that can be used in the context of the invention to prevent or treat dyslipidemia are chosen for example from among the following compounds: 1-oleoyl-2-acetyl-sn-glycerol (OAG), 1-oleoyl-sn-glycerol-3-phosphate (1-oleoyl lysophosphatidic acid or LPA), 2-arachidonoyl glycerol (2-AG), mannide monooleate, 3-hydroxy-2,2-bis(hydroxymethyl)propyl oleate, N,N-diethanololeamide, propylene glycol monooleate, oleic acid monoester with triglycerol and 9-octadecenoic Acid (Z)-(2,2-Dimethyl-1,3-dioxolan-4-yl)methyl ester, and their mixtures.

Preferably, the compounds of interest that can be used in the context of the invention to prevent and/or treat lipotoxicity are chosen from among the following compounds: mannide onooleate, 3-hydroxy-2,2-bis(hydroxymethyl)propyl oleate and N,N-diethanololeamide; alternatively N,N-diethanololeamide; alternatively mannide monooleate, 3-hydroxy-2,2-bis (hydromethyl)propyl oleate, and their mixtures.

One compound of interest particularly preferred to prevent and/or treat lipotoxicity is mannide monooleate.

Alternatively, the compounds of interest that can be used in the context of the invention to prevent and/or treat lipotoxicity are chosen from among: 1-oleoyl glycerol, 2-oleoyl glycerol, glycol monooleate and the oleic acid monoester with triglycerol; preferably propylene glycol monooleate and the oleic acid monoester with triglycerol.

The compounds of interest are used in the context of the invention to prevent and/or treat lipotoxicity such as hypoxic lipotoxicity, typically in restoring the fluidity of the biological membranes. One advantageous characteristic of these compounds is that, unlike the UFAs used in the prior art, they are non-toxic for cells incapable of synthesizing neutral lipids, typically triglycerides and/or esterified sterols. These compounds are especially non-toxic for the pancreatic cells (pancreatic β-cells and pancreatic α-cells). They are also preferably non-toxic for kidney, liver, heart and muscle cells. They are also preferably non-toxic for bronchial epithelial cells. They are moreover preferably advantageously capable of restoring the functions of a lipo-intoxicated cell as well as, if necessary, the functions of the organs involved such as the respiratory tracts and especially the bronchi.

One typical compound of interest of the invention advantageously has the following properties:
- it restores the growth of a mutant hem1Δ of the lipo-intoxicated yeast *Saccharomyces cerevisiae*,
- it reduces or eliminates the UPR (unfolded protein response),
- it is not toxic for a QM mutant of the yeast *Saccharomyces cerevisiae*, and/or
- it reduces or eliminates cell death by apoptosis of lipo-intoxicated mammal cells.

Particular compounds used in the context of the invention are capable of restoring the growth of a mutant hem1Δ of the lipo-intoxicated yeast *Saccharomyces cerevisiae* and/or reduce or eliminate the UPR (unfolded protein response), typically the UPR induced by lipotoxicity (whether endogenous or exogenous).

Particular compounds used in the context of the invention are non-toxic for QM strain yeasts.

Particular compounds used in the context of the invention are capable of reducing or eliminating cell death by apoptosis of lipo-intoxicated mammal cells.

In a preferred embodiment of the invention, the compounds of interest are used to prevent and/or treat pulmonary pathology, particularly a pulmonary pathology leading to respiratory failure, more particularly pulmonary pathology leading to respiratory insufficiency that is cystic fibrosis or COPD.

In a preferred embodiment of the invention, at least one compound of interest as described in the present text is used to prevent and/or treat cystic fibrosis or COPD. The compound mannide monooleate is an example of a compound of interest used preferably to prevent and/or treat cystic fibrosis or COPD.

This at least one compound of interest can be used in one particular embodiment of the invention in combination with a distinct compound known to those skilled in the art and used conventionally to prevent and/or treat cystic fibrosis or COPD, said distinct compound being preferably chosen from among the mucolytic compounds, antibiotics and CFTR protein correctors.

Another object of the invention also relates to a composition taking the form of a pharmaceutical composition, a nutraceutical, a food supplement or complement, comprising at least one compound of interest according to the invention (identified in the present text as a "composition of interest").

One particular object of the invention typically relates to a pharmaceutical composition furthermore comprising said at least one compound of interest according to the invention, at least one other compound (different from the compounds of interest used in the context of the invention to prevent or treat lipotoxicity by hypoxia without inducing toxicity in the non-adipocyte cells) active at the therapeutic level (and recognized as such by those skilled in the art), in particular a compound active in the prevention or treatment of a symptom or an anomaly characteristic of a pulmonary pathology, associated especially with respiratory failure.

The invention also relates to a composition as described in the present text for use to prevent and/or treat lipotoxicity by hypoxia, typically a pathology chosen from among the pulmonary pathologies preferably to prevent and/or treat cystic fibrosis or COPD.

The term "treatment" designates curative, symptomatic or preventive treatment. The compounds of the present invention can thus be used among subjects (such as mammals, especially human beings) affected by an established disease. The compounds of the present invention can also be used to delay or slow down the progress or prevent further progress of the illness, thus improving the condition of the subjects. The compounds of the present invention can also be administered preventively to subjects who are not ill but could normally develop the contract the disease or who have a major risk of contracting the disease.

The compound or compounds of interest or compositions according to the invention can be administered in different ways and in different forms.

Thus, in one typical embodiment, the compound or compounds of interest are administered to the subject, together or separately, and the compound or compounds of interest or compositions according to the invention are administered continuously or sequentially, one or more times per day (daily administration), one or more times per week (weekly administration), or one or more times per month (monthly administration), throughout the duration of the treatment, i.e. until there is improvement in the symptoms of the pathology treated, preferably the disappearance of all or part of the said symptoms.

If necessary, the daily dose can for example be administered in two, three, four, five, six or more doses per day or in multiple sub-doses administered at appropriate intervals during the day.

These compounds or compositions can for example be administered systemically, orally, parenterally, by inhalation or by injection, for example intravenously, intra-peritoneally, by intra-muscular means, subcutaneously, transdermally, by intra-arterial means, etc. For long-term treatment, the preferred mode of administration will be sub-lingual, oral, intra-peritoneal, or transcutaneous.

The compositions can be formulated in the form of injectable suspensions, oils, suppositories, gelules, capsules, sprays, etc., possibly in galenic form or in the form of devices enabling prolonged release and/or delayed release. For injections, the compounds are generally packaged in the form of liquid suspensions which can be injected using, for example, syringes or perfusion.

It is understood that the flow rate and/or the dose injected can be adapted by those skilled in the art depending on the patient, the pathology, the mode of administration, etc. In general, the daily dose of the compound will be the minimum dose needed to obtain the therapeutical effect.

The quantity of compound present in the therapeutic composition can be modulated so as to obtain a circulating level of active substance necessary to obtain the therapeutical effect desired for a particular patient, a composition, a mode of administration, and to do so preferably without toxicity for the patient. The quantity chosen will depend on numerous factors, especially the mode of administration, the duration of administration, the time of administration, the speed of elimination of the compound, of the different product or products used in combination with the compound, the age, the weight and the physical state of the patient as well as his or her medical history and all other information known in medicine.

Typically, the compounds are administered in doses varying from 1 μg to 2 g per administration, preferably 0.1 mg to 1 g per administration. Furthermore, the compositions of the invention can include, in addition, other agents or active substances as explained here above. The compositions of the invention can also include one or more excipients or vehicles, acceptable at the pharmaceutical level. These may be for example saline solutions, physiological solutions, isotonic solutions, buffer solutions, etc., compatible with pharmaceutical use and known to those skilled in the art. The compositions can contain one or more agents or vehicles chosen from among dispersants, solubilizing agents, stabilizing agents, preserving agents, etc.

The invention also relates to methods for preventing or treating lipotoxicity such as hypoxic lipotoxicity in a subject comprising the administration of a compound or a composition of interest, as described in the present text, to prevent and/or treat said lipotoxicity to a subject suffering from lipotoxicity such as hypoxic lipotoxicity or capable of developing lipotoxicity such as hypoxic lipotoxicity.

It also pertains to methods for preventing and/or treating a subject affected by a pathology among the pulmonary pathologies, especially pulmonary pathology leading to respiratory insufficiency, more particularly a pulmonary pathology leading to a respiratory insufficiency that is cystic fibrosis or COPD. These methods include all the steps of administration of a compound or composition of interest, as described in the present text, to prevent and/or treat said pathology, to a subject suffering from such a pathology or liable to develop such a pathology.

The following figures and examples illustrate the invention without limiting its scope.

Following their synthesis, the membrane proteins or secreted proteins (molecular "tools" of the cells) must undergo steps of maturing within the cells. Each of the steps of this process known as the "secretion process" takes place in a specific sub-cell compartment (endoplasmic reticulum (ER) and Golgi apparatus especially). Obtaining mature proteins therefore requires functional intra-cell transport between the different endomembrane systems. This stream is influenced inter alia by the plasticity of the membranes of the intra-cell compartments which is itself directly correlated to the nature of the phospholipids (PL) which form the membranes. In particular, it is accepted that the presence of SFA in PL reduces the membrane fluidity whereas the PLs sheltering UFAs form more fluid membranes.

The beneficial effect of oleic acid (Ole) is observed on the cells having the capacity to buffer an excess exogenous UFAs in the form of neutral liquids (triglycerides (TG) or esterified sterols (SE) stored in a form of lipidic droplets (GL)). In the cells not having this capacity, the surplus exogenous oleic acid ultimately leads to a proliferation of intra-cell membranes in prompting cell stress which will trigger apoptosis.

Figure 1:
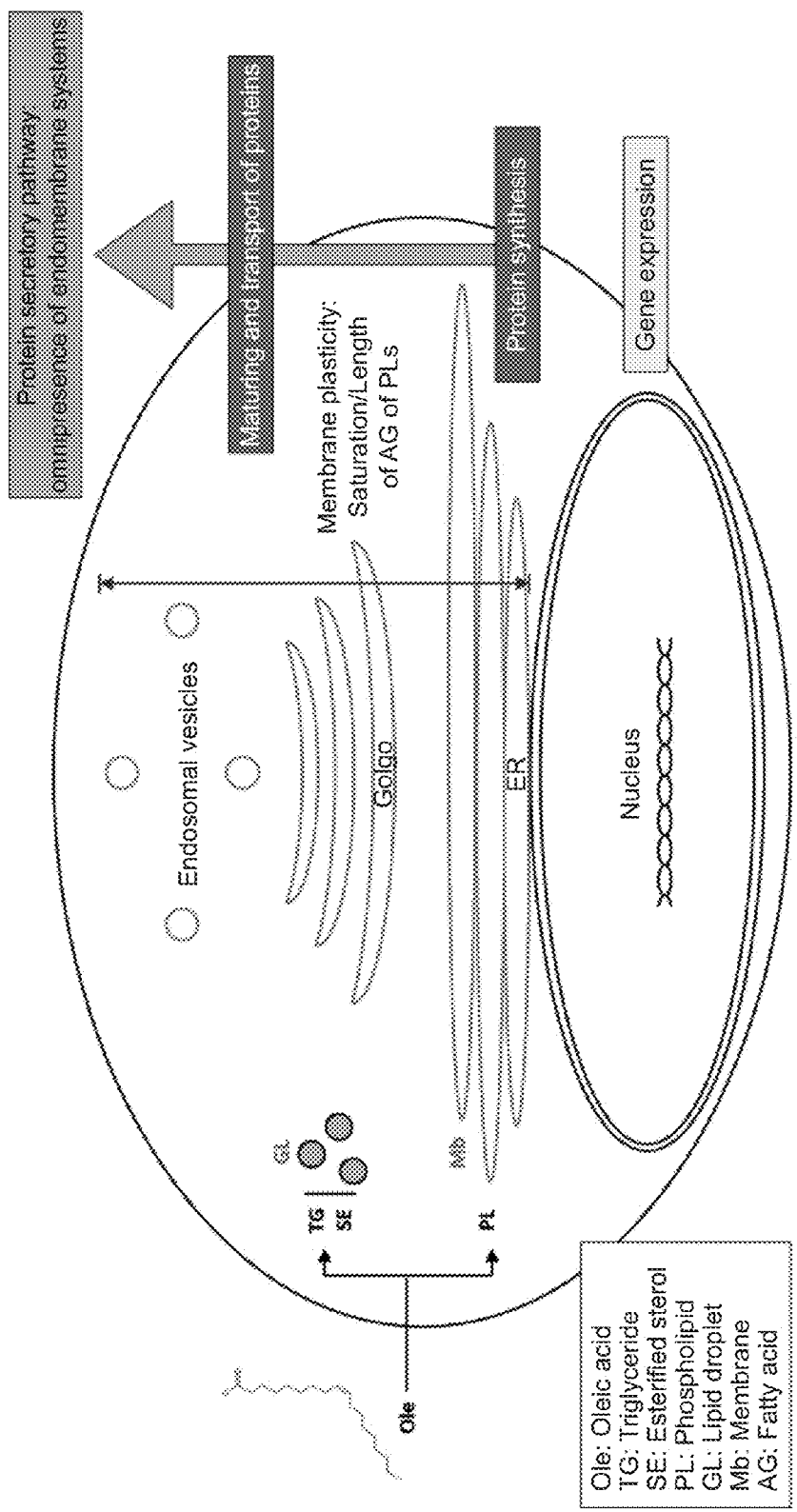
FIG. 1: Secretory pathway and membrane plasticity
Figure 2:
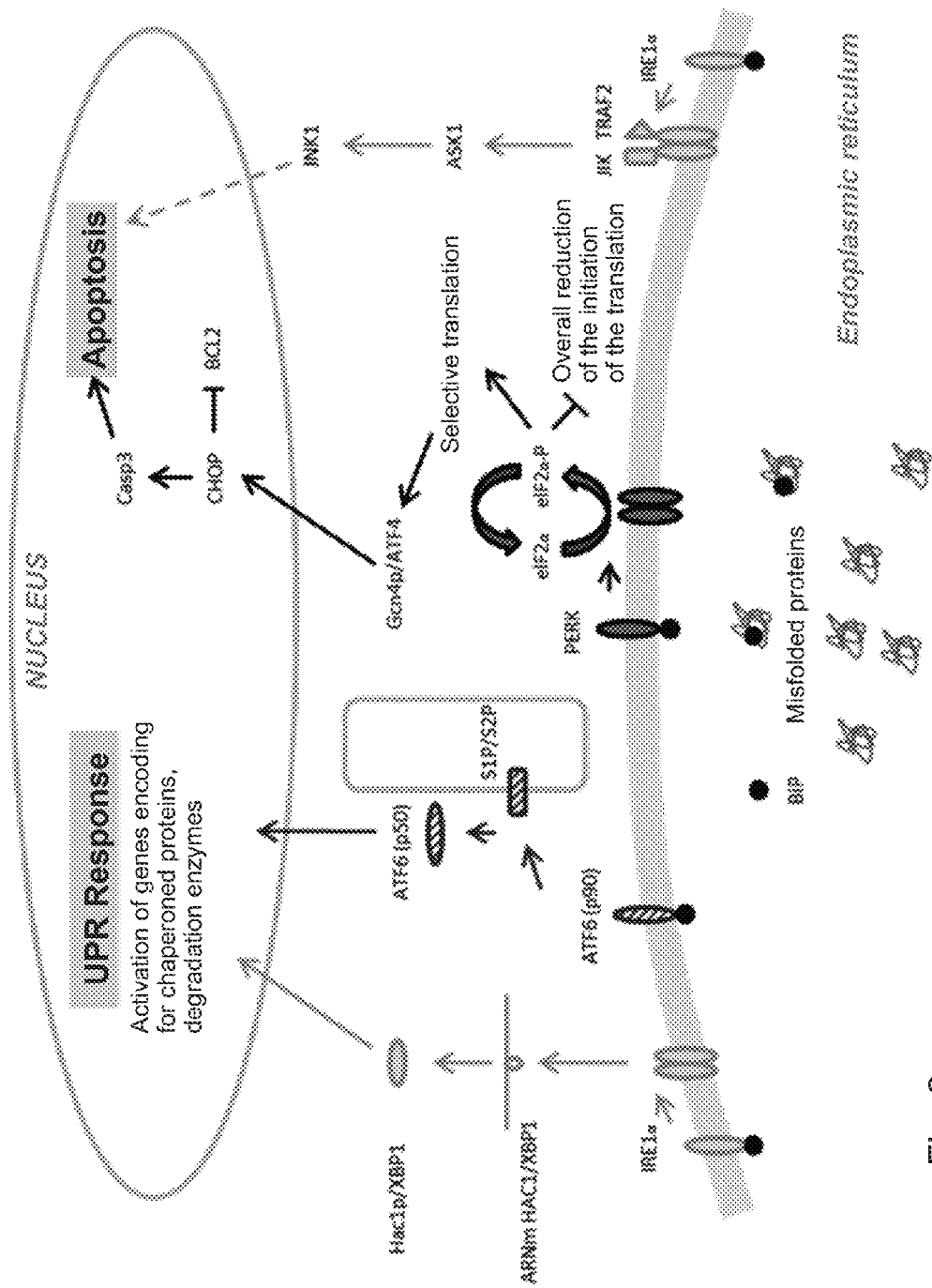

FIG. 2: The UPR pathways in the higher eukaryotes (Pineau & Ferreira, 2010)

Figure 3:
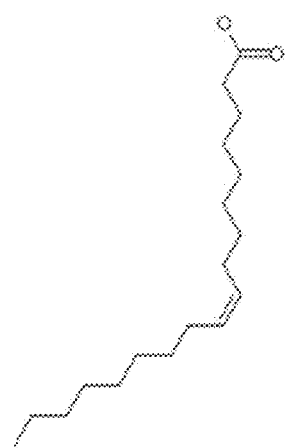
Figure 3:
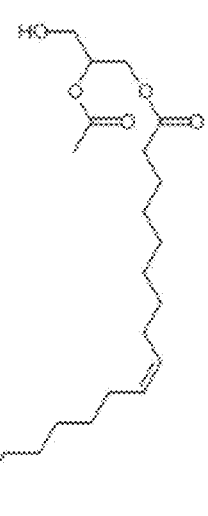
Figure 3:
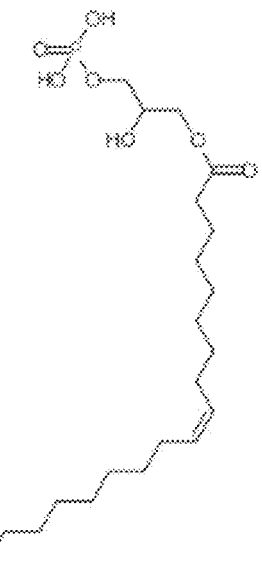
Figure 3:
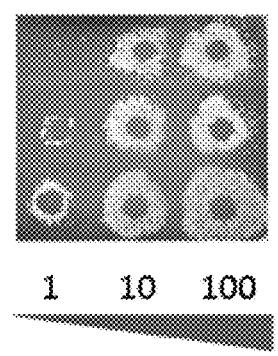

FIG. 3: Oleic acid, OAG and LPA restore the growth of lip o-intoxicated yeasts

FIG. 3A—Structure of oleic acid, OAG and LPA.

FIG. 3B—The hem1Δ yeasts were cultivated in conditions of SFA accumulation as indicated. 5 μl drops of OAG, LPA and oleic acid in the concentrations indicated were then deposited on the surface of the agar medium. The restoration of growth of the hem1Δ yeasts is observed in the formation of colonies after three days.

Figure 4:
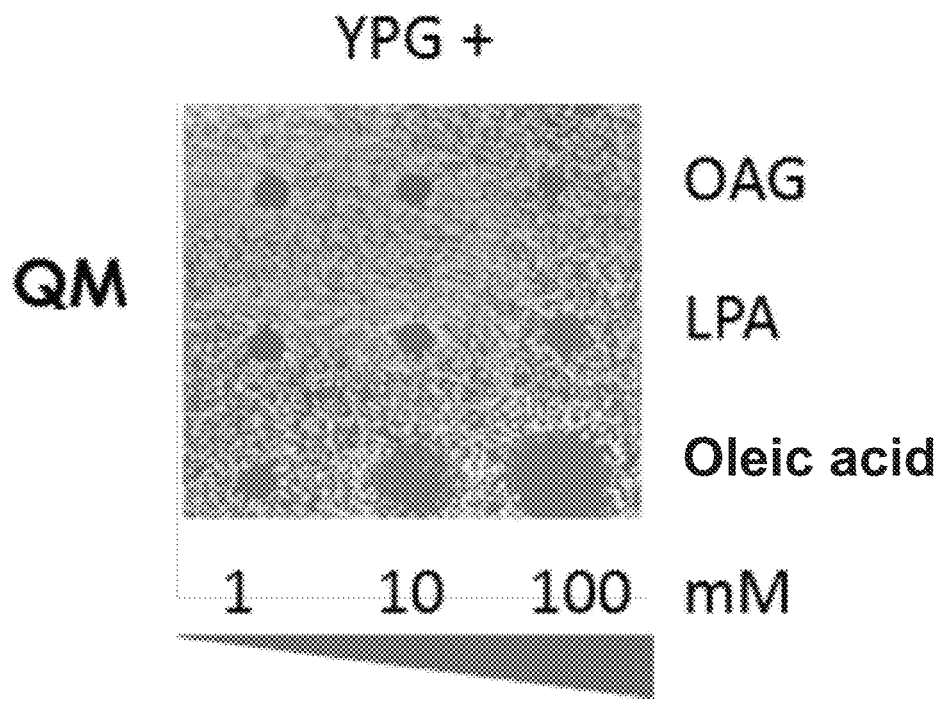

FIG. 4: OAG and LPA are not toxic for cells that do not synthesize triglycerides 5 μl drops of OAG, LPA or oleic acid were deposited, from stock solutions in the concentrations indicated, on the surface of an agar medium on which the QM strain had been preliminarily spread. After three days, haloes of growth inhibition (absence of colonies) can be observed in the case of oleic acid. These haloes are on the contrary not observed in the presence of LPA and OAG.

Figure 5:
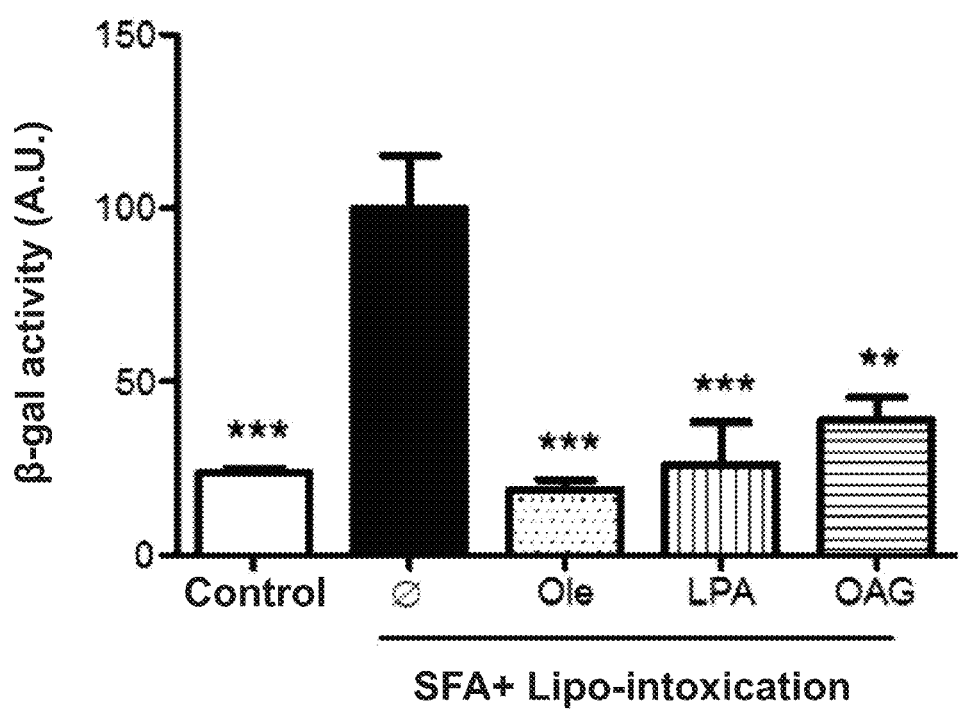

FIG. 5: OAG and LPA reduce the UPR response in lipo-intoxicated yeasts

A plasmidic construction carrying a fusion gene, corresponding to the encoding sequence of the gene LacZ placed under dependence of an artificial promoter containing four UPR elements (UPRE) was introduced into a hem1Δf yeast strain, as described in Pineau et al. (2009). During an induction of the UPR response, the Hac1p/XBP1p transcription is activated and gets fixed on the UPR elements of the fusion gene, leading to the transcription of the LacZ gene. With LacZ encoding β-galactosidase, the level of induction of UPR is measured to detect the corresponding enzyme activity. The hem1Δ yeast strain was cultivated in a liquid medium inducing the accumulation of SFA without other addition (Ø), or in the same medium supplemented with 200 μM of oleic acid, OAG or LPA as indicated. A.U.: arbitrary units.

FIG. 6: OAG does not restore the production of di-unsaturated phospholipids, unlike oleic acid, and LPA, in lipo-intoxicated yeasts.

The hem1Δ yeasts were cultivated in standard conditions (control) or in conditions of SFA accumulation without (Ø) or with the addition of 100 μM of oleic acid, LPA or OAG as indicated.

Figure 6A:
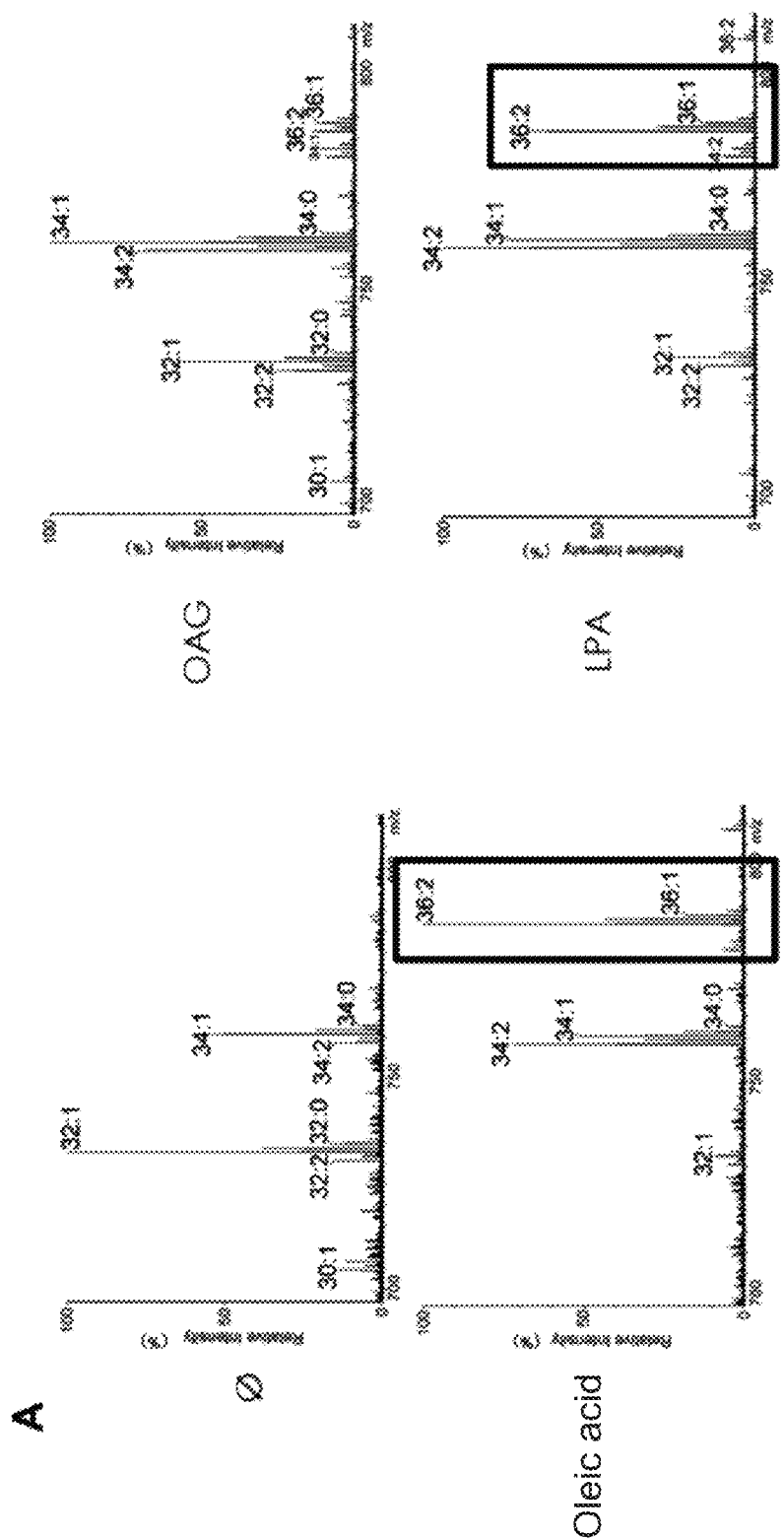

FIG. 6A—After 7 h of incubation, the phospholipids (PL) were extracted and the different species of phosphatidylcholine (PC), which constitute the predominantly present PL were analyzed by mass spectrometry in positive mode, according to Pineau et al. (2008). The species 36:2 corresponding to a PC containing two oleic acid chains was regulated As can be seen, the addition of oleic acid or LPA results in an increase of the level of this species, which is not the case for OAG.

Figure 6B:
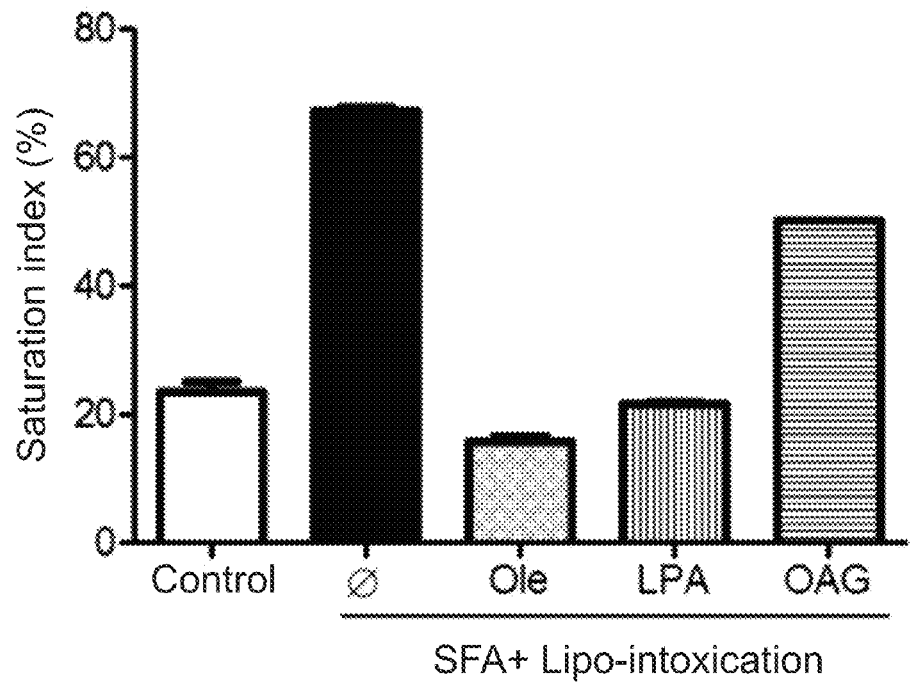

FIG. 6B—All the species of PL detectable in these conditions of mass spectrometry were analyzed to globally quantify the content in SFA forms. The index of saturation thus obtained showed that OAG, unlike oleic acid and LPA, does not restore an index of saturation comparable to the one observed in the control condition.

Figure 7:
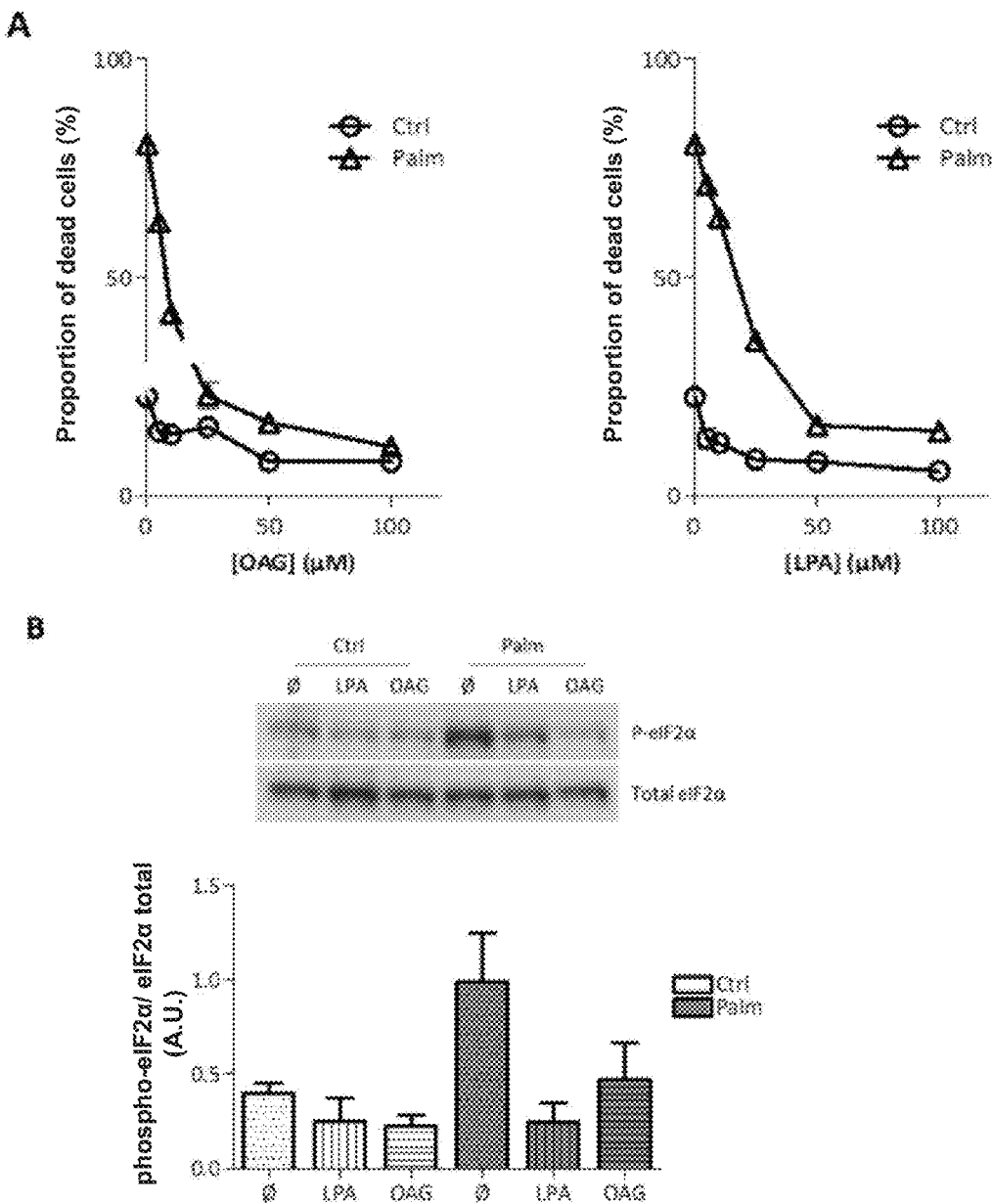

FIG. 7: OAG and LPA prevent apoptosis of the pancreatic β-cells in the presence of saturated fatty acids, in reducing the induction rate of UPR.

The BRIN-BD11 pancreatic β-cells were cultivated in controlled conditions or in the presence of an exogenous source of saturated fatty acids (palmitic acid 200 μM), as described by Dhayal& Morgan (2011) in order to generate conditions of lipotoxicity with or without addition of OAG or LPA.

FIG. 7A—The proportion of dead cells was estimated in the absence (Ctrl) or in the presence of palmitic acid (Palm), for growing concentrations of OAG and LPA.

FIG. 7B—The rates of phosphorylation of eIF2α were also analyzed under different conditions by Western blotting method, in the absence (Ø) or in the presence of OAG or LPA and normalized with quantities of total eIF2α. Since the phosphorylation rate is correlated with the intensity of the UPR response, this experiment shows that OAG reduces the UPR induced by the accumulation of palmitate. A.U.: arbitrary units.

Figure 8:
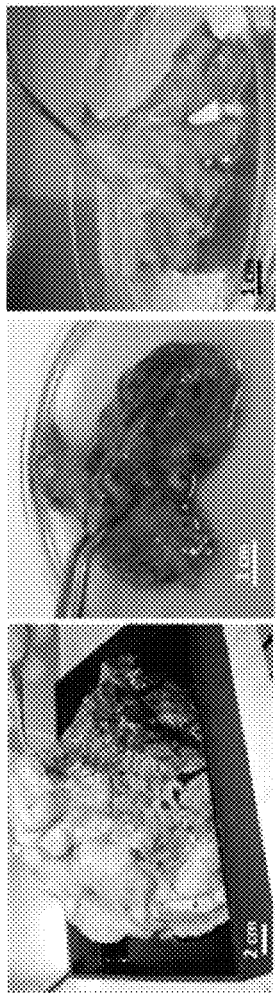
Figure 8:
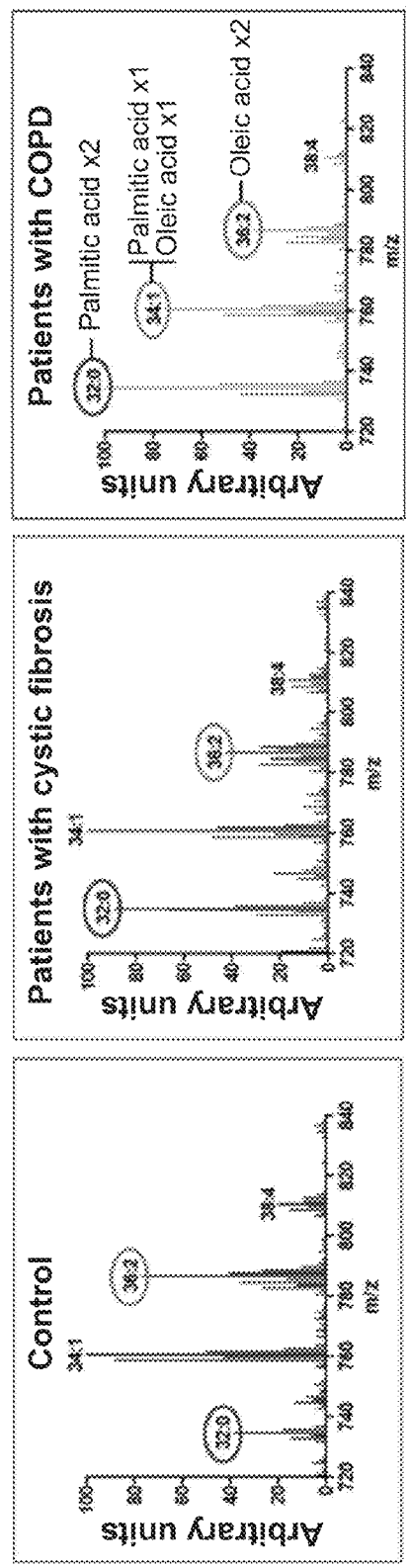

FIG. 8: The bronchial tissues of patients affected by cystic fibrosis or COPD are lipo-intoxicated by SFA.

FIG. 8A—Pulmonary biopsies were dissociated in order to keep only the bronchial component (left to right sequence).

FIG. 8B—The total lipids of the bronchial epithelial cells were extracted, the phospholipids were purified and then the different species of phosphatidylcholine (PC), that constitute the predominantly present PLs were analyzed by mass spectrometry in positive mode according to Pineau et al. (2008). The species 32:0 and 36:2, correspond to PCs containing two palmitic acid chains and two oleic acid chains. As can be seen, the SFA/UFA ratio gets inverted when the PCs from controlled biopsies are compared with PCs from biopsies of patient/s affected by cystic fibrosis or COPD.

Figure 9:
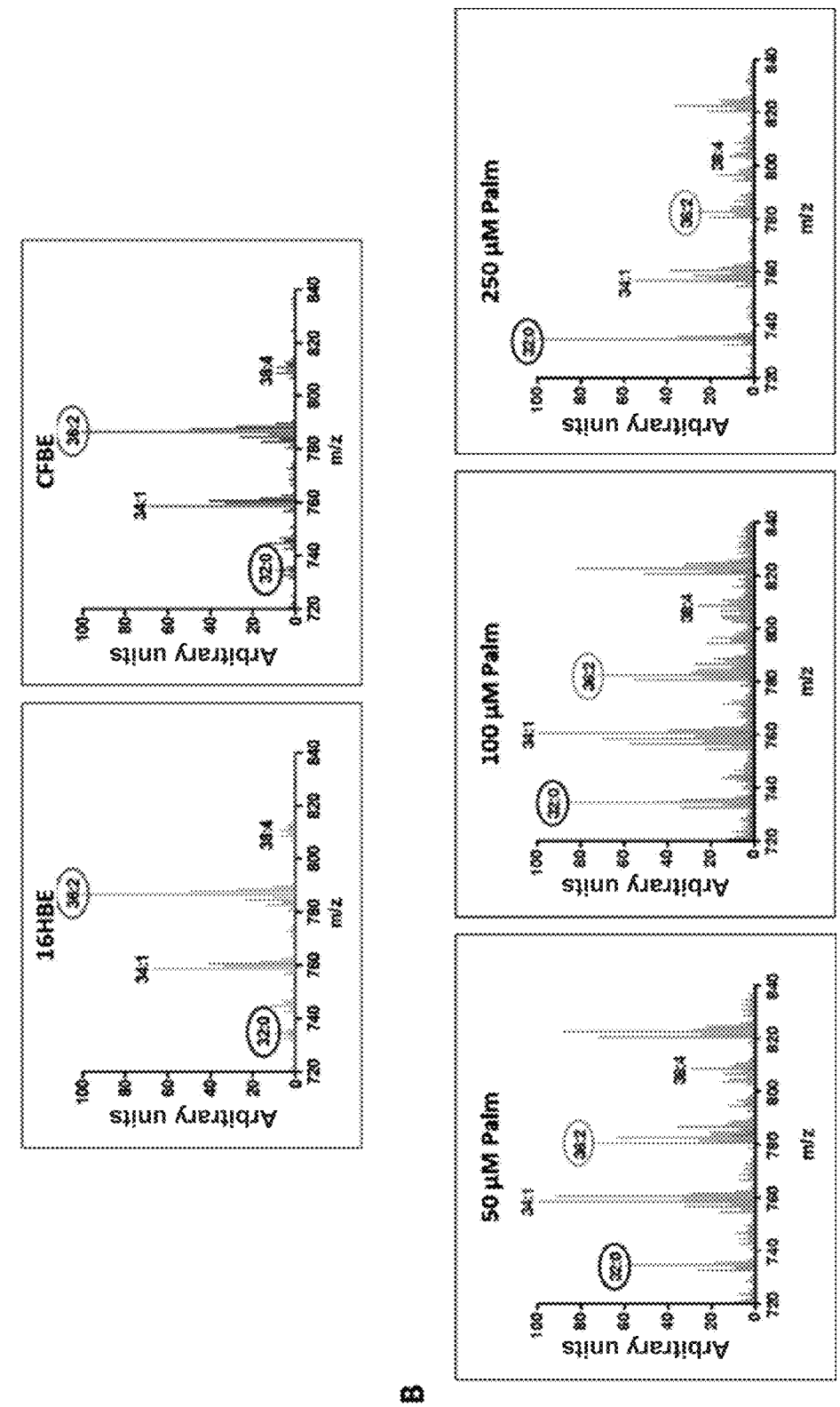

FIG. 9: Induction of lipotoxicity by SFA in bronchial epithelial cell lines, 16HBE and CFBE FIG. 9A—The human bronchial epithelial cell lines, 16HBE and CFBE, were used to test the fatty acid content of their phospholipids in conditions of in vitro culture. Unlike the lipidomic profile observed for pulmonary biopsies of patients with cystic fibrosis or COPD (see FIG. 7B), the SFA/UFA ratio in the PC of the 16HBE and CFBE lines indicate an absence of lipotoxicity.

FIG. 9B—CFBE cells were cultivated for 16 h with increasing quantities of palmitic acid. The analysis of the lipidomic profile of the cells in such conditions reveal that exogenous inputs in SFA mimic the lipotoxicity observed among patients affected by cystic fibrosis (100 µM Palm) or COPD (250 µM Palm).

Figure 10:
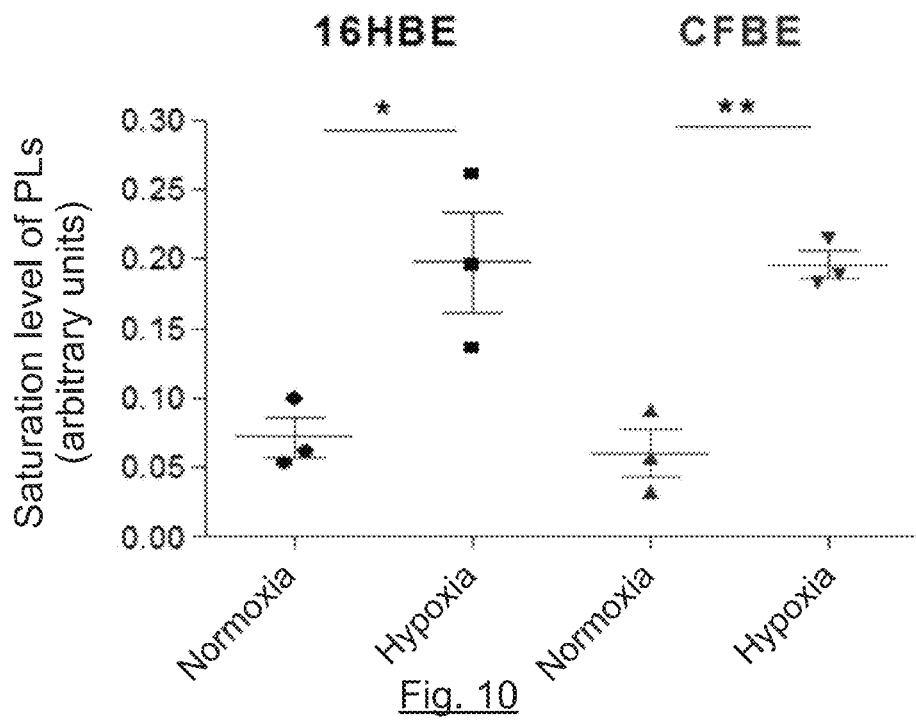

FIG. 10: Conditions of hypoxia induce in vitro the lipotoxicity of the 16HBE and CFBE cell lines artificially reconstituting the hypoxic lipotoxicity observed in the biopsies of patients 16HBE and CFBE were cultivated for 24 h under standard conditions (normoxia: 95% $O_2$+5% $CO_2$) or in an anoxic environment (hypoxia: 95% $N_2$+5% $CO_2$). After extraction of the total lipids and purification of the phospholipids, the overall fatty acid content was analyzed. The SFA/UFA ratios were calculated in order to determine the rates of saturation of phospholipids in each of these conditions. The results indicate that lipotoxicity can be induced in vitro by artificial hypoxia.

Figure 11:
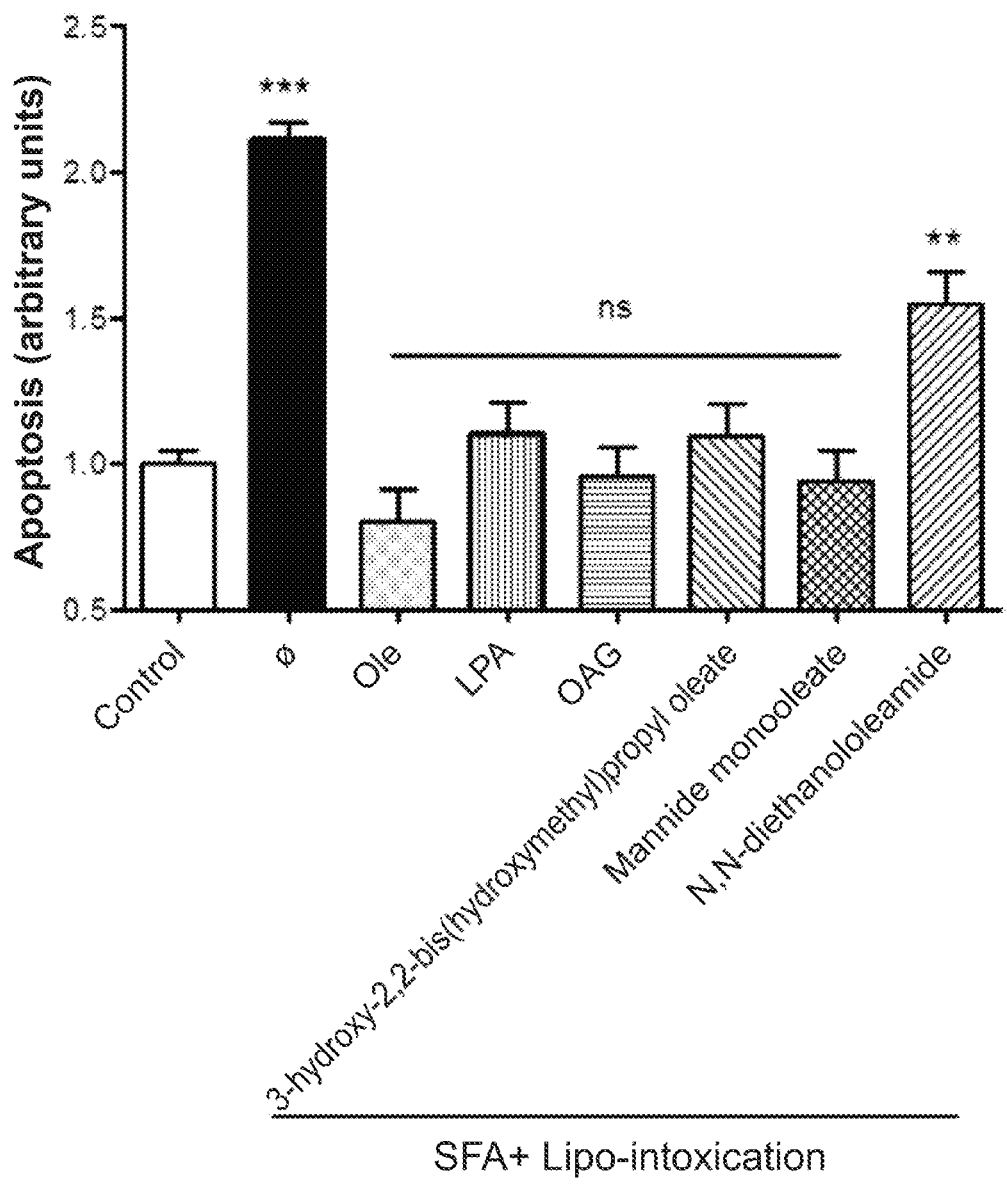

FIG. 11: The anti-SFA compounds against the pro-apoptopic influence of lipotoxicity in bronchial epithelial cells CFBE was cultivated under standard conditions (control) or subjected to a source of exogenous SFA (palmitic acid 250 µM), for 16 h without (Ø) or with the addition of 100 µM of the compounds of interest as indicated. The cells were then lysed and the apoptosis was quantified as indicated in the part entitled "Examples".

Figure 12:
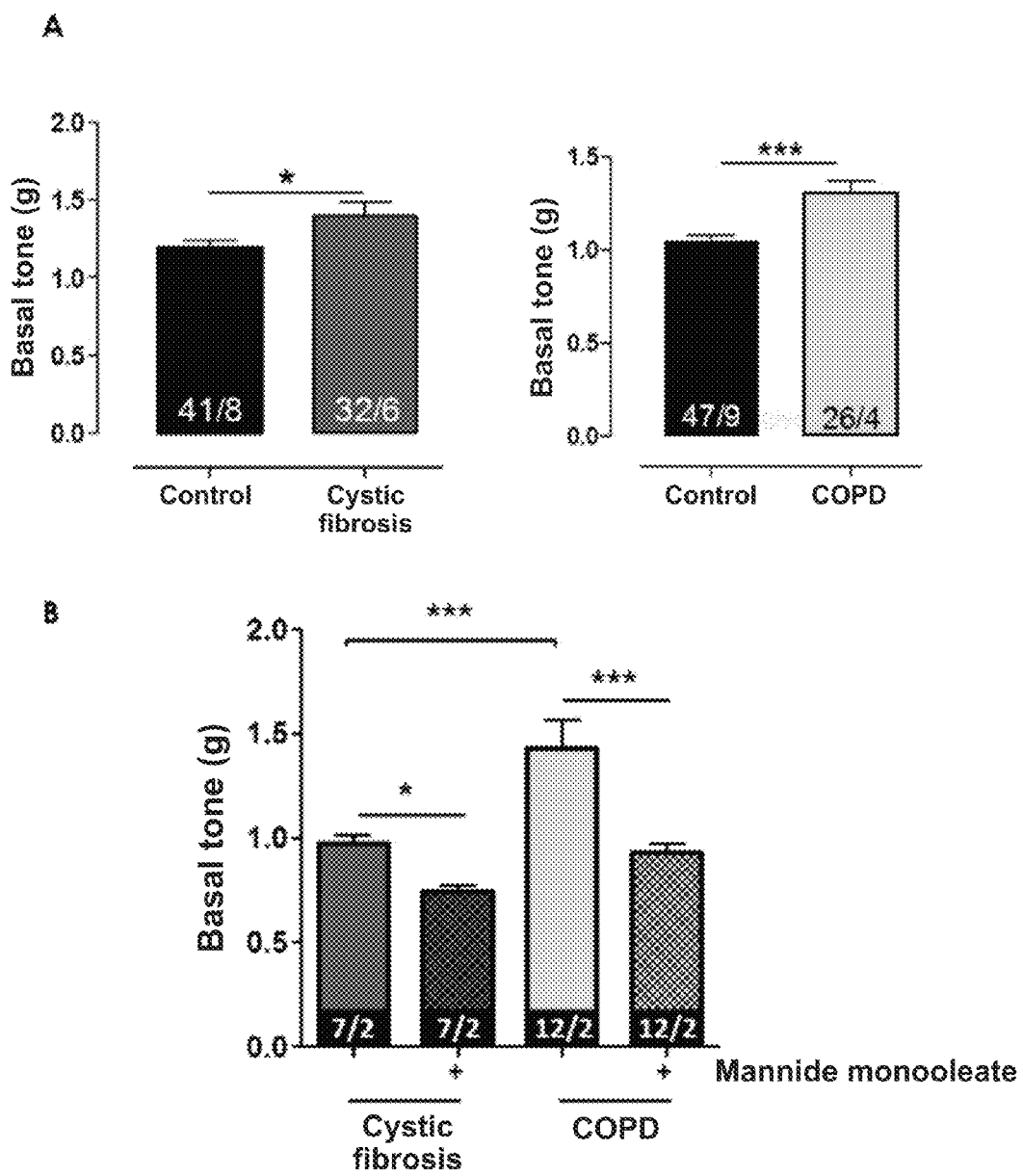

FIG. 12: Mannide monooleate dissipates the bronchial hypertension of the pathological tissues FIG. 12A—Bronchial rings of healthy patients (control), patients affected by cystic fibrosis or chronic obstructive pulmonary disease (COPD) were dissected and then their basic tone was measured. The results show that the two respiratory pathologies are correlated with hypertension of the bronchial tubes.

FIG. 12B—The same operation was carried following a pre-incubation of the rings for 4 h at 37° C. in a physiological solution supplemented (+) or not supplemented with 100 µM of mannide monooleate, as indicated.

For each histogram, a ratio N/n is displayed. N corresponds to the number of rings tested and n to the number of patients analyzed.

EXAMPLES

The invention will be understood more clearly from the following examples:

A/ Yeast Strains, Mammal Cell Lines and Biological Samples

The *Saccharomyces cerevisiae* yeast strains listed in Table 1 are used for the different tests of growth restoration, in order to reveal toxicity, for the analysis of the fatty acid content of the cell phospholipids as well as for the tests for triggering the unfolded protein response (UPR).

The state of activation of UPR and the induction of cell death by lipotoxicity was also analyzed in pancreatic β-cell lines of rats, BRIN-BD11.

Besides, the induction of apoptosis, the secretion of IL-8 and the lipidomic profile in response to lipotoxicity under SFA were also analyzed on human bronchial epithelial cell lines 16HBE (wild homozygote for the CFTR gene) and/or CFBE (homozygote F508del-CFTR).

In addition, ex vivo experiments were performed on biopsies of healthy patients and patients affected by cystic fibrosis or COPD in order to determine the corresponding lipidic profiles as well as the influence of the compounds of interest on the phenomenon of pulmonary hypertension. The uses of biopsies comply with an ethical chart defined by the French equivalent of the Research Ethical Committees called Comité de Protection des Personnes Ouest III or CPP Ouest III.

TABLE 1

Yeast strains used

| Strains | Genotype | Origin |
| --- | --- | --- |
| hem1Δ | MATa trp1 his3 ura3 leu2 hem1::LEU2 | FY1679α × FYHO4 |
| QM (H1246 W303) | MATαare1::HIS3 are2::LEU2 dga1::KanMX4 lro1::TRP1 ADE2 ura3 | ScanBi Ltd., Alnarp, Sweden |
| WT (G175 W303) | MATa ADE2 MET his3 leu2 ura3 trp1 | ScanBi Ltd., Alnarp, Sweden |

B/ Lipotoxicity of Hem1Δ Yeasts

The strain carrying the hem1Δ strain is cultivated, under aerobic conditions, under stirring and at 28° C., in a $YPG^-$ liquid medium (YPG (yeast extract 1% (m/v), peptone 1% (m/v) and glucose 2% (m/v)) supplemented with δ-aminolevulinic acid (ALA) at 80 µg/mL). Lipotoxicity by saturated fatty acids (SFA) is prompted by depletion of unsaturated fatty acids (UFA)—the synthesis of which is dependent on the presence of haem (prosthetic grouping of the enzyme Ole1p especially)—by transfer into $YPG^+$ medium (YPG supplemented with ergosterol at 80 µg/mL to compensate for the depletion in sterol obtained under these conditions). The lipotoxicity can be induced in a solid medium $YPG^+$+agar 2% (m/v) in transferring 3500 cells (hem1Δ coming from a pre-culture in $YPG^-$)/cm² or *alternatively in a liquid medium in inoculating $2 \cdot 10^6$ cells/mL of $YPG^+$. Classically, the effects of lipotoxicity on SFA are analyzed 7 h after the transfer into $YPG^+$ medium. The capacity of a compound to counter the deleterious effects of lipotoxicity with SFA is for its part evaluated successively with the addition of this compound on (or in) the $YPG^+$ transfer medium after seeding with cells.

C/ Lipotoxicity of Pancreatic β-Cells of Rats by Palmitic Acid

1) Preparation of Lipidic Reagents:

The lipidic species are prepared in ethanol and then complexed with bovine serum albumen (BSA initially devoid of fatty acids) by incubation for one hour at 37° C. The stock of palmitate is obtained by the addition of a volume of ethanol before the entire mixture is heated to 70°

C. for homogenization. OAG and LPA solutions are prepared in ethanol 100% at ambient temperature. For incubation of mammal cells, the final concentrations of BSA and ethanol in the culture medium are respectively kept at 1% and 5% (m/v).

2) Tests of Cell Viability:

The pancreatic β-cell cell line (BRIN-BD11) of rats is cultivated in an RPMI-1640 complete medium containing glucose at 11 mM and supplemented with 10% (v/v) of fetal calf serum (FCS), 2 mM of L-glutamine, 100 U/mL of penicillin and 100 μg/mL of streptomycin. For each experiment, the cells are initially seeded at a density of $0.5 \times 10^5$ cells/mL in six-well dishes for 24 h. The full medium was then replaced by an equivalent devoid of FCS but containing a lipidic reagent of interest, in desired concentrations, complexed with BSA. In the case of the controlled conditions, identical quantities of BSA and ethanol were then used. At the end of the incubations, all the cells (dead and living) are collected and centrifuged at 300 g for 5 minutes. The cell wall was then put into suspension in 200 μL of medium and then the DNA of the dead cells (having lost the integrity of the plasma membrane) was marked with propidium iodide (PI) by adding 200 μL of a solution of PI at 20 μg/mL in FACS buffer (phosphate-buffered saline (PBS), 2% (v/v) FCS, sodium azide 10 mM). After incubation at 10 minutes on ice, the samples thus obtained are analyzed by cytometry in flux. A Beckman Coulter EPICS XL MCL is used for quantification, an FL3 channel serves to detect emissions from PI interposed in the DNA and the analysis is done by means of the software EXPO32 ADC (Applied Cytometry Systems, V 1.1 build 207).

3) Western Blotting:

The cells BRIN-BD11 are seeded at a density of $0.5 \times 10^5$ cells/mL in T25 flasks for 24 h. As indicated here above, the complete medium is then replaced by an equivalent devoid of FCS but containing the lipid reagents of interest. After 6 h of incubation, the extraction of the total proteins is done by means of a lysis buffer (Tris 20 mM, NaCl 150 mM, EDTA 1 mM and Triton-X 1% (v/v)) containing protease and phosphate inhibitors. These proteins are then subjected to electrophoresis in acrylamide gel 12% NuPAGE® Novex® Bis-Tris Gels (Invitrogen) and then transferred to a PVDF membrane and then probed by means of the antibody anti-phospho eIF2α (Cell Signalling (New England Biolabs)) diluted to $1/1000^{th}$. In a second stage, the membranes are stripped with the buffer Re-Blot Plus-Strong (Millipore) and then probed a second time with total anti-eIF2α antibodies (CellSignalling (New EnglandBiolabs) diluted to $1/1000^{th}$. The analysis by densitometry of the relative abundance of the phosphorylated and non-phosphorylated forms of the protein eIF2α is done with the Fluor-S Multi-imager analysis system combined with the software program Quantify One (Biorad UK Ltd).

D/ Restoration of Growth

1) Screening of compounds: Following the induction of lipotoxicity with SFA (for hem1Δ cultivated in a solid medium), 5 μL drops of solutions of different compounds at 10 mM in dimethylsulfoxide (DMSO) or in ethanol (EtOH) are deposited on the surface of agar. The capacity of a compound to counter the lipo-induced stoppage of cell growth is estimated by the appearance of a halo of hem1Δ colonies at the position of the deposit of said compound after three days of culture at 28° C. (cf. Deguil et al., 2011).

2) Kinetics of proliferation: Conjointly with the induction of lipotoxicity with SFA (for hem1Δ yeasts in liquid medium), different compounds are added to the cultures at an initial concentration of 200 μM. The tracking of the proliferation is done by measuring the cell density by spectrometry at regular time intervals (every hour for the duration of the observation). At a wavelength of 600 nm, a unit of optical density ($DO_{600\ nm}$) corresponds to $2 \cdot 10^7$ cells/mL.

E/ Toxicity Test

At the same time, wild strains (WT) and QM are cultivated in aerobic conditions under stirring and at 28° C., in a YPG liquid medium before seeding 3500 cells per $cm^2$ of YPG+agar 2% (m/v). Following this transfer to solid medium, 1 μL drops of solutions of different compounds at 1, 10 and 100 mM in DMSO or EtOH are deposited on the surface of the agar. Separately, deposits of DMSO and EtOH are also made in order to assess the intrinsic toxicity of these two solvents. After three days of culture of 28° C., the toxicity of the tested compounds is evaluated by comparing the diameters of the growth inhibition haloes obtained for the deposits of undissolved solvents with those of the deposits of different concentrations of compounds tested. Contrary to the WTstrain, the QM strain is incapable of buffering an excess of exogenous oleic acid in the form of neutral lipids (triglycerides (TG) or sterol esters (SE)) in lipid droplets. Thus, in the case of an absence of toxicity relative to the WT strain, the observation of a toxicity of a compound relative to the QM strain indicates that this compound is perceived as a source of free fatty acid by the yeasts.

F/ Extraction of Total Lipids

The hem1Δ strain is cultivated in a $YPG^A$, $YPG^+$ or $YPG^+$ liquid medium+200 μM of compound to be tested in aerobic conditions, under stirring and at 28° C. for 7 h, starting from an initial cell concentration of $2 \cdot 10^6$ cells/mL. At the end of the culture, $10^8$ cells are collected in order to carry out the extraction of the total lipids. After the cells have been put in suspension in 1 mL of distilled water at 4° C., 500 μL of glass beads (Ø 0.6 mm) are added and the whole mixture then undergoes three sequences of 20 seconds at 5000 rpm in a stirrer (the tubes are kept on ice between each of the three sequences). The cellular lysate then obtained, complemented with water for rinsing the beads (1 mL), is then transferred into a 40 mL glass tube (Corex™) and then the lipids are extracted by using a methanol:chloroform ratio of 2:1 (v/v). Initially, 6 mL of methanol are added and the entire mixture is vortexed for 30 seconds and then incubated for 15 minutes at 65° C. Once the mixture has been cooled to ambient temperature, 300 mL of chloroform is added and then the entire mixture is again vortexed for 30 seconds before allowing the extraction to take place for 16 h. Subsequently, the sample is centrifuged for 12 minutes at 10000 g and then the supernatant is transferred into a new Corex™ tube. After the addition of 2 mL of chloroform and then 4 mL of distilled water, the entire mixture is vortexed for 30 seconds and then centrifuged for 8 minutes at 3000 g. After elimination of the resultant upper phase, the lower organic phase is collected in a hemolysis tube made of glass. Finally, the solvent is evaporated under a nitrogen stream at 80° C. to obtain total cell lipid samples.

In the case of biopsies on patients, after dissection of the pulmonary lobes and extraction of the bronchi, the bronchial epithelial cells were rinsed three times in PBS and then the total lipids were prepared as indicated here above, starting from $10^5$ cells.

G/ Purification of Phospholipids and Analysis by Mass Spectrometry

The samples of total cell lipids are put back into suspension in 1 mL of dichloromethane in being vortexed for 30 seconds. The entire mixture is deposited on a silica column (BOND ELUT-SI, 100 mg 1 mL) preconditioned with 3 mL of methanol and then 2 mL of dichloromethane successively. The fraction retained by the column is then washed with 2 mL of dichloromethane and then 2 mL of acetone successively. Finally, 2 mL of a mixture of chloroform/methanol/water 50:45:5 (v/v/v) are deposited on the column and the phospholipids thus eluted are collected in a glass hemolysis tube. The solvent is evaporated under nitrogen at 80° C. to obtain the samples of cellular phospholipids.

Once put back into suspension in 100 µL of mixture Mix⁻ (isopropanol/acetonitrile/water 2:1:1 (v/v/v)+triethylamine 1% (v/v)) or mixture Mix⁺ (isopropanol/acetonitrile/water 2:1:1 (v/v/v)+formic acid 1% (v/v)), the samples are analyzed by mass spectrometry (Electro Spray Ionization-Mass Spectrometry (ESI-MS)) in negative or positive mode respectively and the results obtained serve to analyze the fatty acid content of the different species of phospholipids.

H/ UPR Triggering Test

The hem1Δ strain transformed by the plasmid pPW344 [2 µ URA34×UPRE-LacZ (Patil et al., 2004)] is cultivated in liquid medium $YPG^A$, YPG or YPG+200 µM of compound to be tested in aerobic conditions, under stirring and at 28° C. for 7 h, starting from an initial cell concentration of $2 \cdot 10^6$ cells/mL. At the end of the culture, $10^8$ cells are collected in order to quantify the beta-galactosidase (β-gal) activity resulting from the expression of the LacZ trans gene (in the case of a triggering of UPR). In a first stage, the cells are put back into suspension in 1.5 mL of buffer Z ($Na_2HPO_4$ at 60 mM, $NaH_2PO_4$ at 40 mM, KCl at 10 mM, $MgSO_4$ at 1 mM and β-mercaptoethanol at 50 mM; solution at pH 7) then $1/15^{th}$ of this suspension is used to carry out a measurement of $DO_{600\ nm}$. In a second stage, the suspension is complemented with 100 µL of sodium dodecyl sulphate (SDS) 0.1% (v/v) and 200 µL of chloroform then vortexed in two successive sequences of 30 seconds. After decantation (settling), 400 µL (volume V) of the solution thus obtained is transferred into a glass hemolysis tube and then complemented with 600 µL of buffer Z. 200 µL of ortho-nitrophenyl-β-galactoside (ONPG) substrate, at 4 mg/mL in the buffer Z is then added before the entire mixture becomes homogenized by vortex then incubated at 30° C. in a waterbath at 30° C. to initiate the reaction. When the entire mixture has a slightly yellowish color, the reaction is interrupted (at the time t) at ambient temperature by the addition of 500 µL of $Na_2CO_3$ at 1M. Finally, after the samples have been centrifuged for 5 minutes at 800 g and then the supernatants have been collected in the new glass hemolysis tubes, the products of the reaction (o-nitrophenol) as well as the cell debris are dosed by spectrometry at the wavelengths 420 and 550 nm respectively. For each sample, the activity β-gal (U) is computed using the formula U=(1000× $[DO_{420\ nm}-(1.75\times DO_{550nm})])/(t\times DO_{600nm}.)$, expressed in arbitrary units.

I/ Lipotoxicity In Vitro of Bronchial Epithelial Cell Lines, 16HBE and CFBE

1) Lipotoxicity by exogenous palmitic acid. As with what has been presented here above for BRIN-BD 11, 16HBE and CFBE are cultivated in MEM supplemented by 5 µg/mL of plasmocine and 10% (v/v) of horse serum, at 37° C. and then exposed to palmitic acid concentrations of 50, 100 or 250 µM for 16 h. Then the consequences of the exogenous lipotoxicity are tested.

2) Hypoxic lipotoxicity. In standard way, the 16HBE and the CFBE are sustained in conditions of normoxia. In this way, the cells are sustained in a chamber fed with a mixture formed by 95% of $O_2$ and 5% of $CO_2$. In the conditions of induction of hypoxia, the cells are subjected for 48 h to an anoxic gas mixture comprising 95% of $N_2$ and 5% of $CO_2$, and then the consequences of the lipotoxicity known as hypoxic lipotoxicity are tested.

3) Apoptosis test. Under conditions of exogenous lipotoxicity, the induction of apoptosis was analyzed by the use of the cell death detection kit ELISA$^{PLUS}$ (ROCHE). The CFBE are seeded in a 96-well dish at a concentration of 10000 cells per well. At the end of 16 h of lipotoxicity, the cells are lysed and the apoptosis is measured, according to the given instructions, by quantification of cytoplasmic oligonucleosomes which reveal DNA deterioration associated with apoptosis.

J/ Measurement of Bronchial Basal Tone.

After dissection of the pulmonary lobes, bronchial rings are isolated and mounted on a device for analysis by the technique of isolated organs, in which they are immersed in a KREBS physiological buffer. Following the stabilization of the tone of the circles, the basal tone is measured. As an alternative, the rings are incubated for 4 h in an additional KREBS buffer of 100 µM of mannide mono-oleate.

REFERENCES

Alkhateeb H, Chabowski A, Glatz J F C, Luiken J F P, Bonen A (2007) Two phases of palmitate-induced insulin resistance in skeletal muscle: impaired GLUT4 translocation is followed by a reduced GLUT4 intrinsic activity. *American Journal of Physiology—Endocrinology And Metabolism* 293: E783-E793

Bigay J, Casella J F, Drin G, Mesmin B, Antonny B. ArfGAP1 responds to membrane curvature through the folding of a lipid packing sensor motif. EMBO J. 2005 Jul. 6; 24(13):2244-53.

Boslem E, MacIntosh G, Preston A M, Bartley C, Busch A K, Fuller M, Laybutt D R, Meikle P J, Biden T J. A lipidomic screen of palmitate-treated MIN6 β-cells links sphingolipid metabolites with endoplasmic reticulum (ER) stress and impaired protein trafficking. Biochem J. 2011 Apr. 1; 435(1):267-76.

Butler A E, Janson J, Bonner-Weir S, Ritzel R, Rizza R A, Butler P C. (2003) β²-Cell Deficit and Increased β²-Cell Apoptosis in Humans With Type 2 Diabetes. Vol. 52, pp. 102-110.

Cnop M, Hannaert J C, Hoorens A, Eizirik D L, Pipeleers D G (2001) Inverse Relationship Between Cytotoxicity of Free Fatty Acids in Pancreatic Islet Cells and Cellular Triglyceride Accumulation. Diabetes 50: 1771-1777.

Cunha D A, Hekerman P, Ladriere L, Bazarra-Castro A, Ortis F, Wakeham M C, Moore F, Rasschaert J, Cardozo A K, Bellomo E, Overbergh L, Mathieu C, Lupi R, Hai T, Herchuelz A, Marchetti P, Rutter G A, Eizirik D L, Cnop M. (2008) Initiation and execution of lipotoxic ER stress in pancreatic {beta}-cells. Vol. 121, pp. 2308-2318.

Deguil J, Pineau L, Rowland Snyder E C, Dupont S, Beney L, Gil A, Frapper G, Ferreira T (2011) Modulation of Lipid-Induced ER Stress by Fatty Acid Shape. *Traffic* 12: 349-362

Dhayal S, Morgan N G (2011) Structure-activity relationships influencing lipid-induced changes in eIF2alpha phosphorylation and cell viability in BRIN-BD11 cells. *FEBS Lett* 585: 2243-2248

Diakogiannaki E, Morgan N G. (2008) Differential regulation of the ER stress response by long-chain fatty acids in the pancreatic β-cell. Vol. 036, pp. 959-962.

Diakogiannaki E, Welters H J, Morgan N G. (2008) Differential regulation of the endoplasmic reticulum stress response in pancreatic {beta}-cells exposed to long-chain saturated and monounsaturated fatty acids. Vol. 197, pp. 553-563.

Egnatchik R A, Leamy A K, Jacobson D A, Shiota M, Young J D. ER calcium release promotes mitochondrial dysfunction and hepatic cell lipotoxicity in response to palmitate overload. Mol Metab. 2014 May 22; 3(5):544-53.

Guo W, Wong S, Xie W, Lei T, Luo Z. (2007) Palmitate modulates intracellular signaling, induces endoplasmic reticulum stress, and causes apoptosis in mouse 3T3-L1 and rat primary preadipocytes. Vol. 293, pp. E576-586.

Kato T, Shimano H, Yamamoto T, Ishikawa M, Kumadaki S, Matsuzaka T, Nakagawa Y, Yahagi N, Nakakuki M, Hasty A H, Takeuchi Y, Kobayashi K, Takahashi A, Yatoh S, Suzuki H, Sone H, Yamada N. (2008) Palmitate Impairs and Eicosapentaenoate Restores Insulin Secretion Through Regulation of SREBP-1c in Pancreatic Islets. Vol. 57, pp. 2382-2392.

Katsoulieris E, Mabley J G, Samai M, Green I C, Chatterjee P K (2009) [alpha]-Linolenic acid protects renal cells against palmitic acid lipotoxicity via inhibition of endoplasmic reticulum stress. *European Journal of Pharmacology* 623: 107-112

Kincaid M M, Cooper A A (2007) ERADicate ER Stress or Die Trying. *Antioxid Redox Signal*

Kirby E F, Heard A S, Wang X R. Enhancing the Potency of F508del Correction: A Multi-Layer Combinational Approach to Drug Discovery for Cystic Fibrosis. J Pharmacol Clin Toxicol. 2013 Aug. 28; 1(1):1007.

Kohlwein S D, Petschnigg J (2007) Lipid-induced cell dysfunction and cell death: lessons from yeast. *Current hypertension reports* 9: 455-461

Laybutt D R, Preston A M, Akerfeldt M C, Kench J G, Busch A K, Biankin A V, Biden T J (2007) Endoplasmic reticulum stress contributes to beta cell apoptosis in type 2 diabetes. *Diabetologia* 50: 752-763

Listenberger L L, Han X, Lewis S E, Cases S, Farese R V, et al. (2003) Triglyceride accumulation protects against fatty acid-induced lipotoxicity. PNAS 100: 3077-3082

Patil C K, Li H, Walter P. Gcn4p and novel upstream activating sequences regulate targets of the unfolded protein response. PLoS Biol. 2004 August; 2(8):E246

Payet L A, Pineau L, Snyder E C, Colas J, Moussa A, Vannier B, Bigay J, Clarhaut J, Becq F, Berjeaud J M, Vandebrouck C, Ferreira T. Saturated fatty acids alter the late secretory pathway by modulating membrane properties. Traffic. 2013 Sep. 6

Pedemonte N, Lukacs G L, Du K, Caci E, Zegarra-Moran O, Galietta L J, Verkman A S. Small-molecule correctors of defective DeltaF508-CFTR cellular processing identified by high-throughput screening. J Clin Invest. September; 115(9):2564-71. 2005

Petschnigg J, Moe O W, Stagljar I (2011) Using yeast as a model to study membrane proteins. *Current opinion in nephrology and hypertension* 20: 425-432

Petschnigg J, Wolinski H, Kolb D, Zellnig G n, Kurat C F, Natter K, Kohlwein S D (2009) Good Fat, Essential Cellular Requirements for Triacylglycerol Synthesis to Maintain Membrane Homeostasis in Yeast. *J Biol Chem* 284: 30981-30993

Pineau L, Bonifait L, Berjeaud J-M, Alimardani-Theuil P, Berges T, Ferreira T (2008) A Lipid-mediated Quality Control Process in the Golgi Apparatus in Yeast. *Mol Biol Cell* 19: 807-821

Pineau L, Colas J, Dupont S, Beney L, Fleurat-Lessard P, Berjeaud J M, Berges T, Ferreira T (2009) Lipid-Induced ER Stress: Synergistic Effects of Sterols and Saturated Fatty Acids. *Traffic*

Pineau L, Ferreira T (2010) Lipid-induced ER stress in yeast and β cells: parallel trails to a common fate. *FEMS Yeast Research*

Poon P P, Nothwehr S F, Singer R A, Johnston G C. The Gcs1 and Age2 ArfGAP proteins provide overlapping essential function for transport from the yeast trans-Golgi network. J Cell Biol. 2001 Dec. 24; 155(7):1239-50

Robinson M, Poon P P, Schindler C, Murray L E, Kama R, Gabriely G, Singer R A, Spang A, Johnston G C, Gerst J E. The Gcs1 Arf-GAP mediates Snc1,2 v-SNARE retrieval to the Golgi in yeast. *Mol Biol Cell.* 2006 April; 17(4):1845-58

Sampson H M, Robert R, Liao J, Matthes E, Carlile G W, Hanrahan J W, Thomas D Y. Identification of a NBD1-binding pharmacological chaperone that corrects the trafficking defect of F508del-CFTR. Chem Biol. February 25; 18(2):231-42. 2011

Schneider M F, Marsh D, Jahn W, Kloesgen B, Heimburg T. Network formation of lipid membranes: triggering structural transitions by chain melting. Proc Natl Acad Sci USA. 1999 Dec. 7; 96(25):14312-7

Stein D T, Stevenson B E, Chester M W, Basit M, Daniels M B, Turley S D, McGarry J D (1997) The insulinotropic potency of fatty acids is influenced profoundly by their chain length and degree of saturation. *The Journal of Clinical Investigation* 100: 398-403

Van Goor F, Straley K S, Cao D, Gonzalez J, Hadida S, Hazlewood A, Joubran J, Knapp T, Makings L R, Miller M, Neuberger T, Olson E, Panchenko V, Rader J, Singh A, Stack J H, Tung R, Grootenhuis P D, Negulescu P. Rescue of DeltaF508-CFTR trafficking and gating in human cystic fibrosis airway primary cultures by small molecules. Am J Physiol Lung Cell Mol Physiol. June; 290(6):L1117-30. 2006

Van Goor F, Hadida S, Grootenhuis P D, Burton B, Stack J H, Straley K S, Decker C J, Miller M, McCartney J, Olson E R, Wine J J, Frizzell R A, Ashlock M, Negulescu P A. Correction of the F508del-CFTR protein processing defect in vitro by the investigational drug VX-809. Proc Natl Acad Sci USA. November 15; 108(46):18843-8. 2011

Wang Y, Bartlett M C, Loo T W, Clarke D M. Specific rescue of cystic fibrosis transmembrane conductance regulator processing mutants using pharmacological chaperones. Mol Pharmacol. July; 70(1):297-302. 2006

Wei Y, Wang D, Topczewski F, Pagliassotti M J. (2006) Saturated fatty acids induce endoplasmic reticulum stress and apoptosis independently of ceramide in liver cells. Vol. 291, pp. E275-281.

Zhang K, Kaufman R J. (2006) The unfolded protein response: A stress signaling pathway critical for health and disease. Vol. 66, pp. S102-109.

Vachel L, Norez C, Becq F, Vandebrouck C. Effect of VX-770 (ivacaftor) and OAG on Ca2+ influx and CFTR activity in G551D and F508del-CFTR expressing cells. J. Cyst. Fibros. 2013 December; 12(6):584-91.

The invention claimed is:

1. A method for treating a subject with cystic fibrosis or chronic obstructive pulmonary disease, comprising the step of administering to said subject a composition comprising mannide monooleate.

2. The method according to claim 1, characterized in that the compound administered to the subject is non-toxic for cells capable of synthesizing neutral lipids.

3. The method according to claim 1, where the subject is an animal.

4. The method according to claim 1, wherein the compound is formulated as a composition being chosen from among a pharmaceutical composition and a nutraceutical or food supplement.

5. The method according to claim 1, wherein the composition further comprises N,N-diethanololeamide.

6. The method according to claim 1, wherein the composition further comprises 3-hydroxy-2,2-bis (hydromethyl) propyl oleate.

7. The method according to claim 2, characterized in that the compound administered to the subject is non-toxic for cells capable of synthesizing triglycerides and/or esterified sterols.

8. The method according to claim 7, characterized in that the compound administered to the subject is non-toxic for bronchial epithelial cells.

9. The method according to claim 1, wherein the subject has cystic fibrosis.

10. The method according to claim 1, where the subject is a mammal.

11. The method according to claim 1, where the subject is a human being.

12. The method according to claim 1, wherein the subject has chronic obstructive pulmonary disease.

* * * * *